United States Patent
Chae et al.

(10) Patent No.: US 10,793,589 B2
(45) Date of Patent: Oct. 6, 2020

(54) RESORCINARENE-BASED AMPHIPATHIC COMPOUND AND USE THEREOF

(71) Applicant: Industry-University Cooperation Foundation Hanyang University Erica Campus, Ansan-si (KR)

(72) Inventors: Pil Seok Chae, Ansan-si (KR); Hazrat Hussain, Swabi (PK)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 0 days.

(21) Appl. No.: 16/344,852

(22) PCT Filed: Mar. 17, 2017

(86) PCT No.: PCT/KR2017/002871
§ 371 (c)(1),
(2) Date: Apr. 25, 2019

(87) PCT Pub. No.: WO2018/079951
PCT Pub. Date: May 30, 2018

(65) Prior Publication Data
US 2020/0102341 A1 Apr. 2, 2020

(30) Foreign Application Priority Data
Oct. 28, 2016 (KR) .................. 10-2016-0141870

(51) Int. Cl.
*C07H 15/18* (2006.01)
*G01N 21/76* (2006.01)
*G01N 33/68* (2006.01)

(52) U.S. Cl.
CPC ............ *C07H 15/18* (2013.01); *G01N 21/76* (2013.01); *G01N 33/6842* (2013.01)

(58) Field of Classification Search
None
See application file for complete search history.

(56) References Cited

FOREIGN PATENT DOCUMENTS

| WO | WO 2004/036315 | 4/2004 | |
|---|---|---|---|
| WO | WO 2015/158575 | 10/2015 | |
| WO | WO-2015158575 A1 * | 10/2015 | ............. C07H 15/24 |
| WO | WO 2018/079951 | 5/2018 | |

OTHER PUBLICATIONS

International Search Report and the Written Opinion dated Jul. 17, 2017 From the International Searching Authority Re. Application No. PCT/KR2017/002871 and Its Translation of Search Report Into English. (9 Pages).
Curtis "Novel Calix[4]Resorcinarene Glycosides", Tetrahedron Letters, 38(24): 4295-4296, Jun. 16, 1997.
Husain et al. "Spatially Directional Resorcin[4]Arene Cavitand Glycoconjugates for Organic Catalysis", Chemistry—A European Journal, 22(18): 6223-6227, Published Online Mar. 21, 2016.
Newstead et al. "Insights Into Outer Membrane Protein Crystallization", Molecular Membrane Biology, 25(8): 631-638, Dec. 2008.
Newstead et al. "Rationalizing Alpha-Helical Membrane Protein Crystallization", Protein Science, 17(3): 466-472, Mar. 2008.
Sakamizu et al. "Structural Design of Resin Matrix and Acid-Lebile Dissolution Inhibitor of Chemical Amplification Positive Electron-Beam Resist for Gigabit Lithography", Journal of Photopolymer Science and Technology, 11(4): 547-552, 1998.

* cited by examiner

*Primary Examiner* — Traviss C McIntosh, III

(57) ABSTRACT

The present invention relates to a newly developed resorcinarene-based amphipathic compound, a method for producing the same, and a method for extracting, solubilizing, stabilizing, crystallizing, or analyzing a membrane protein by using the same. In addition, compared to a conventional compound, the compound can efficiently extract, from a cell membrane, membrane proteins having a greater variety of structures and characteristics, and can stably store such membrane proteins for a long time in an aqueous solution. Therefore, the compound can be used to analyze the functions and structures of such membrane proteins. Analysis of the structures and functions of membrane proteins, being closely related to the development of new drugs, is one of the fields of greatest interest in biology and chemistry today.

15 Claims, 11 Drawing Sheets

FIG. 4A
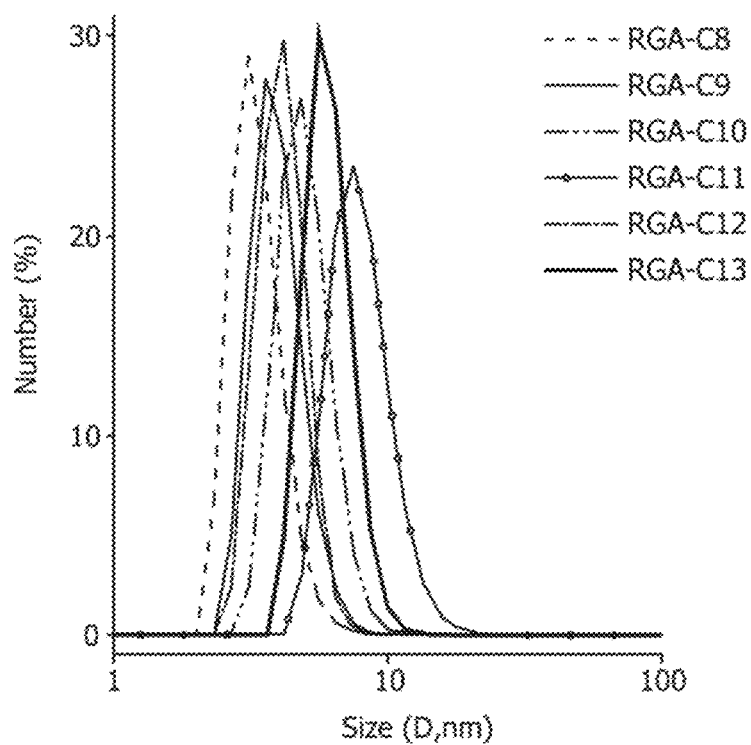
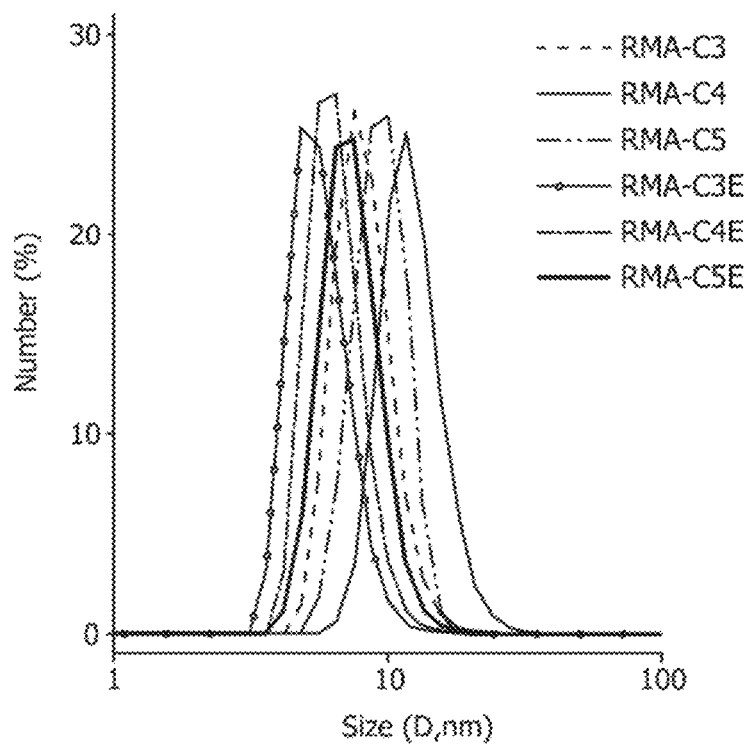
FIG. 4B

FIG. 10A
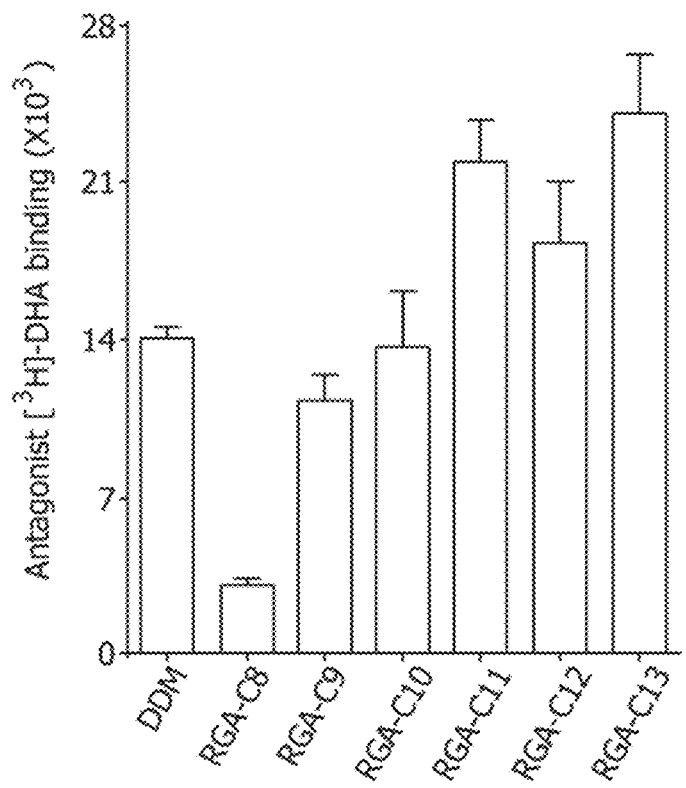
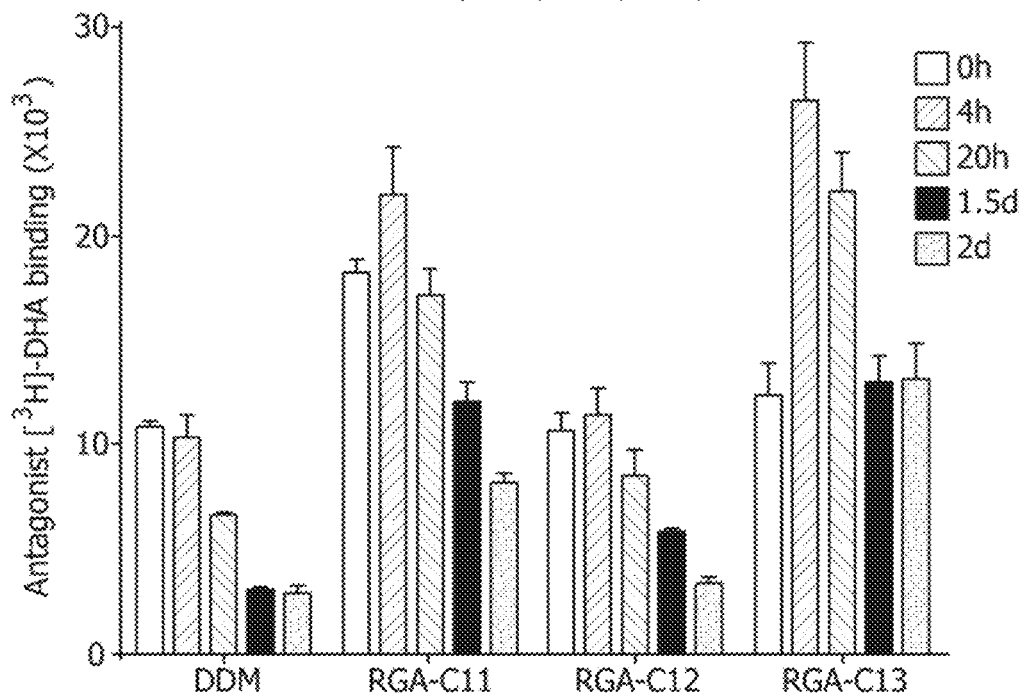
FIG. 10B

FIG. 12A
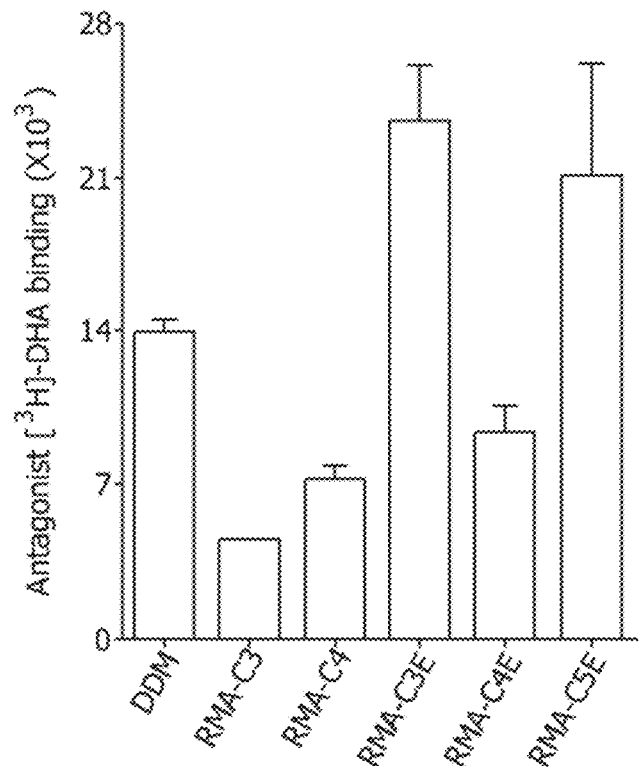
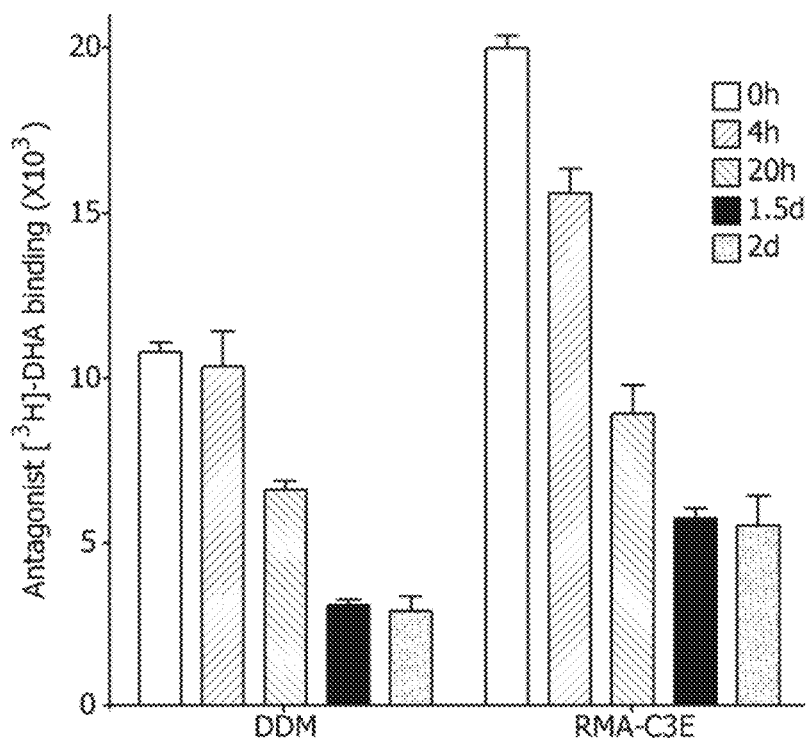
FIG. 12B

RESORCINARENE-BASED AMPHIPATHIC COMPOUND AND USE THEREOF

RELATED APPLICATIONS

This application is a National Phase of PCT Patent Application No. PCT/KR2017/002871 having International filing date of Mar. 17, 2017, which claims the benefit of priority of Korean Patent Application No. 10-2016-0141870 filed on Oct. 28, 2016. The contents of the above applications are all incorporated by reference as if fully set forth herein in their entirety.

FIELD AND BACKGROUND OF THE INVENTION

The present invention relates to a newly developed resorcinarene-based amphipathic compound, a method of preparing the same, and a method of extracting, solubilizing, stabilizing, crystallizing, or analyzing a membrane protein by using the same.

Membrane proteins perform important functions in biological systems. Since these bio-macromolecules include hydrophilic and hydrophobic parts, an amphipathic molecule is needed to extract the membrane proteins from a cell membrane and solubilize and stabilize the same in an aqueous solution.

To analyze the structure of a membrane protein, a high-quality membrane protein crystal should be obtained. To accomplish this, the structural stability of a membrane protein in an aqueous solution should be prioritized. Although 100 or more existing amphipathic molecules have been used in research on membrane proteins, about five amphipathic molecules thereamong have been actively utilized in membrane protein structure research. The five amphipathic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (Non-Patent Documents 1 and 2). However, the structures of membrane proteins surrounded by these molecules are easily denatured or agglomerated, thereby rapidly losing functions thereof. Accordingly, there are considerable limitations in performing research on the functions and structures of membrane proteins using these molecules. This problem occurs because the chemical structures of existing molecules are simple and, accordingly, do not allow the exhibition of various characteristics of the membrane proteins. Therefore, there is a need for the development of a novel amphipathic material that has a novel structure and thus exhibits superior characteristics.

Therefore, the present inventors developed a novel amphipathic compound in which hydrophobic and hydrophilic groups are introduced into a resorcinarene-centered structure, and found a membrane protein stabilization characteristic of this compound, thus completing the present invention.

(Non-Patent Document 1) S. Newstead et al., Protein Sci. 17 (2008) 466-472.

(Non-Patent Document 2) S. Newstead et al., Mol. Membr. Biol. 25 (2008) 631-638.

SUMMARY OF THE INVENTION

The present invention has been made in view of the above problems, and it is an objective of the present invention to provide a compound represented by Formula 1 or Formula 2.

It is another objective of the present invention to provide a composition for extracting, solubilizing, stabilizing, crystallizing, or analyzing a membrane protein, which includes the above-described compound.

It is still another objective of the present invention to provide a method of preparing the above-described compound.

It is yet another objective of the present invention to provide a method of extracting, solubilizing, stabilizing, crystallizing, or analyzing a membrane protein by using the above-described compound.

Technical Solution

In accordance with an aspect of the present invention, there is provided a compound represented by the following Formula 1 or Formula 2:

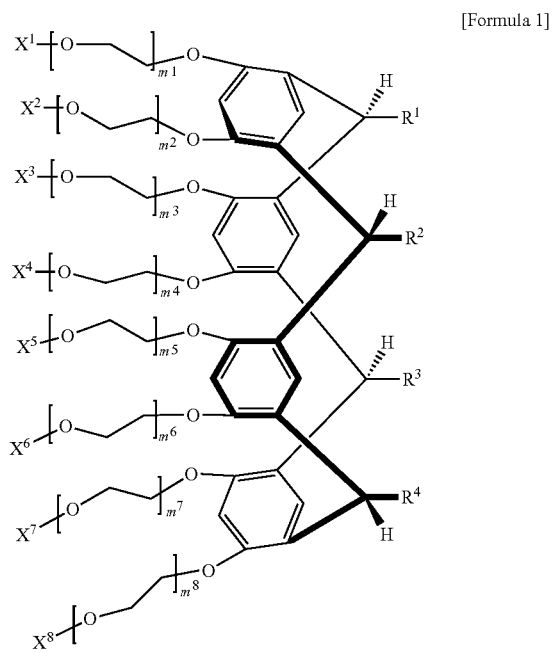

[Formula 1]

In Formula 1, $R^1$ to $R^4$ may be each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^8$ may be saccharides; and $m^1$ to $m^8$ may be 0, 1, or 2.

[Formula 2]

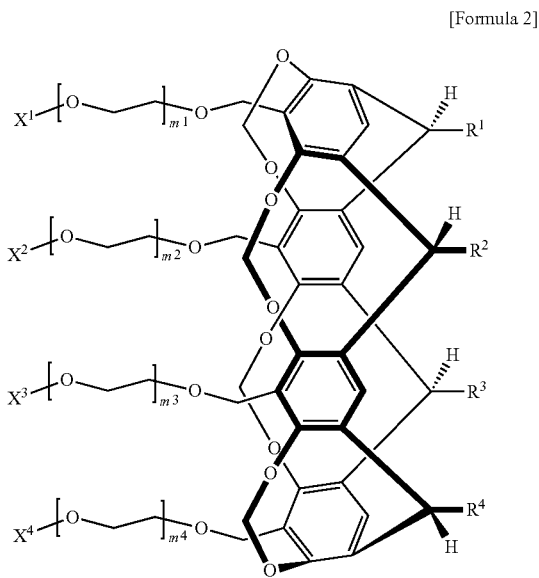

In Formula 2, $R^1$ to $R^4$ may be each independently a substituted or unsubstituted $C_2$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^4$ may be saccharides; and $m^1$ to $m^4$ may be 0, 1, or 2.

The term "saccharide" used herein refers to a compound whose molecular size is relatively small compared to other carbohydrates, and which is sweet when dissolved in water. Saccharides are classified into monosaccharides, disaccharides, and polysaccharides depending on the number of molecules constituting the saccharide.

The saccharide used in the embodiment may be a monosaccharide or a disaccharide. Specifically, the saccharide may be glucose or maltose, but the present invention is not limited thereto.

The saccharide may function as a hydrophilic group. The compound according to an embodiment of the present invention is prepared by connecting two saccharides, as hydrophilic groups, in parallel to minimize an increase in length while enlarging the size of hydrophilic groups and thus the size of a complex of the saccharides and a membrane protein is reduced. When the complex of the compound and the membrane protein is small, a high-quality membrane protein crystal may be obtained (G. G. Prive, *Methods* 2007, 41, 388-397).

In addition, $R^1$ to $R^4$ may function as hydrophobic groups. To attain optimal hydrophile-lipophile balance (HLB), four hydrophobic groups are introduced into the compound according to an embodiment of the present invention.

The compound according to an embodiment of the present invention may have a resorcinarene linker formed by aldol condensation of four resorcinol compounds as a centered linker. That is, the compound is an amphipathic material in which four or eight hydrophilic groups and four hydrophobic groups are introduced into a resorcinarene-centered structure formed by aldol condensation of four resorcinol compounds, and may exhibit excellent stabilization and crystallization of a membrane protein.

Specifically, $R^1$ to $R^4$ may be each independently a substituted or unsubstituted alkyl group described hereinabove; and $X^1$ to $X^8$ may be glucoses or maltoses. According to an embodiment of the present invention, in Formula 1, $R^1$ to $R^4$ may be each independently a substituted or unsubstituted $C_3$-$C_{30}$ alkyl group; $X^1$ to $X^8$ may be glucoses; and $m^1$ to $m^8$ may be 1. The resultant compounds may be referred to as "resorcinarene-based glucosides (RGAs)". According to another embodiment of the present invention, in Formula 2, $R^1$ to $R^4$ may be each independently a substituted or unsubstituted $C_2$-$C_{30}$ alkyl group; $X^1$ to $X^4$ may be maltoses; and $m^1$ to $m^4$ may be 0, 1, or 2. The resultant compounds may be referred to as "resorcinarene-based maltosides (RMAs)".

In an embodiment of the present invention, a compound represented by Formula 1, wherein $R^1$ to $R^4$ are $C_7$ alkyl groups; $X^1$ to $X^8$ are glucoses; and $m^1$ to $m^8$ are 1, is referred to as "RGA-$C_8$". Accordingly, the compound may be a compound represented by the following Formula 3:

[Formula 3]

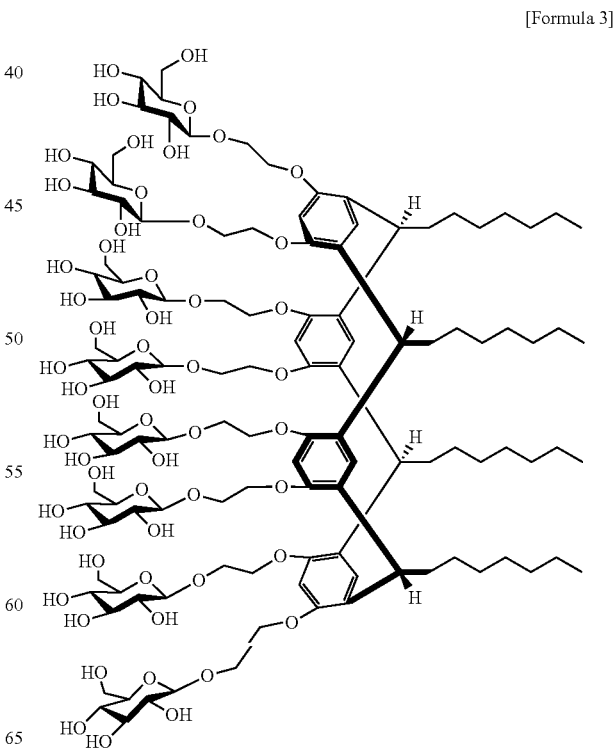

In an embodiment of the present invention, a compound represented by Formula 1, wherein $R^1$ to $R^4$ are $C_8$ alkyl groups; $X^1$ to $X^8$ are glucoses; and $m^1$ to $m^8$ are 1, is referred to as "RGA-$C_9$". Accordingly, the compound may be a compound represented by the following Formula 4:

[Formula 4]

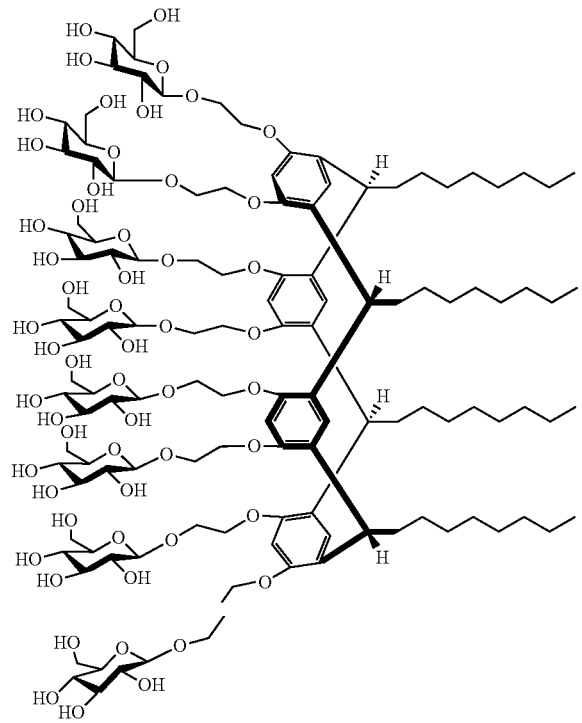

In an embodiment of the present invention, a compound represented by Formula 1, wherein $R^1$ to $R^4$ are $C_9$ alkyl groups; $X^1$ to $X^8$ are glucoses; and $m^1$ to $m^8$ are 1, is referred to as "RGA-C10". Accordingly, the compound may be a compound represented by the following Formula 5:

[Formula 5]

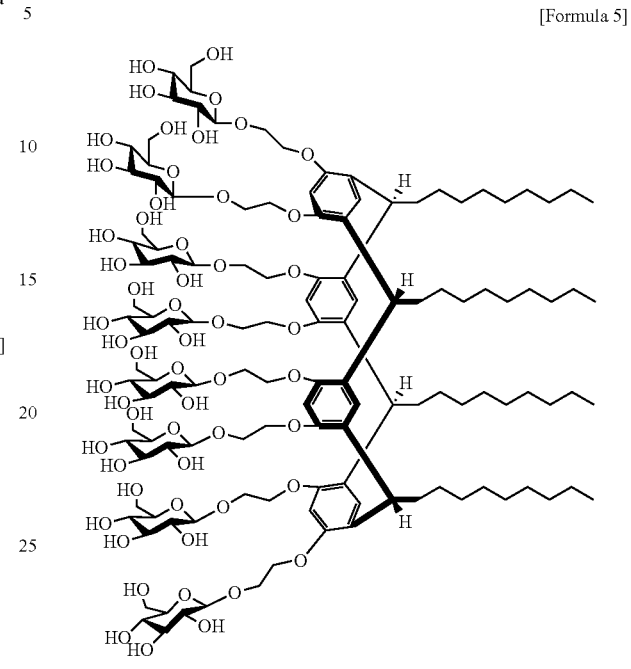

In an embodiment of the present invention, a compound represented by Formula 1, wherein $R^1$ to $R^4$ are $C_{10}$ alkyl groups; $X^1$ to $X^8$ are glucoses; and $m^1$ to $m^8$ are 1, is referred to as "RGA-C11". Accordingly, the compound may be a compound represented by the following Formula 6:

[Formula 6]

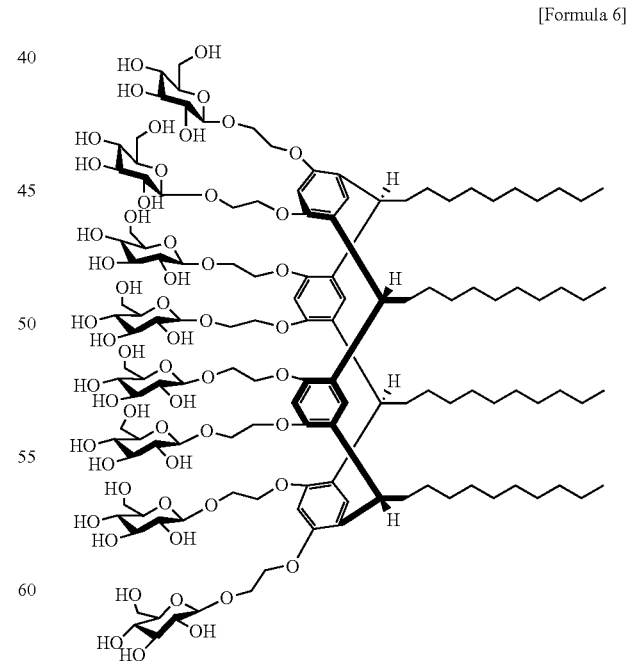

In an embodiment of the present invention, a compound represented by Formula 1, wherein $R^1$ to $R^4$ are $C_{11}$ alkyl groups; $X^1$ to $X^8$ are glucoses; and $m^1$ to $m^8$ are 1, is referred to as "RGA-C12". Accordingly, the compound may be a compound represented by the following Formula 7:

[Formula 7]

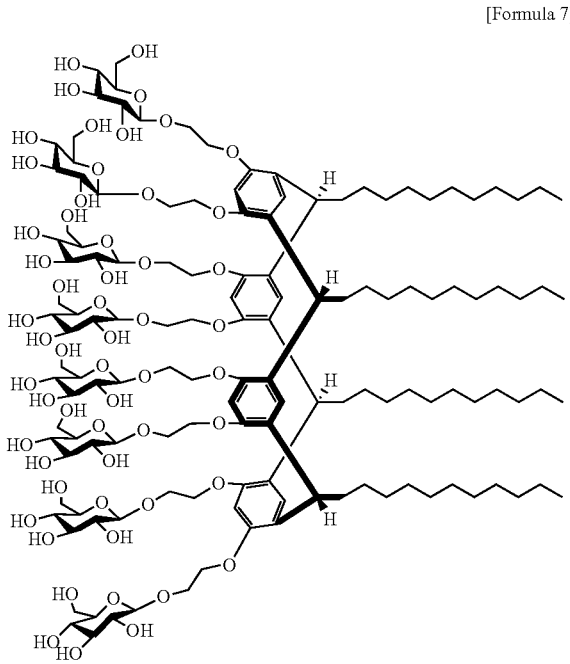

In an embodiment of the present invention, a compound represented by Formula 1, wherein $R^1$ to $R^4$ are $C_{12}$ alkyl groups; $X^1$ to $X^8$ are glucoses; and $m^1$ to $m^8$ are 1, is referred to as "RGA-C13". Accordingly, the compound may be a compound represented by the following Formula 8:

[Formula 8]

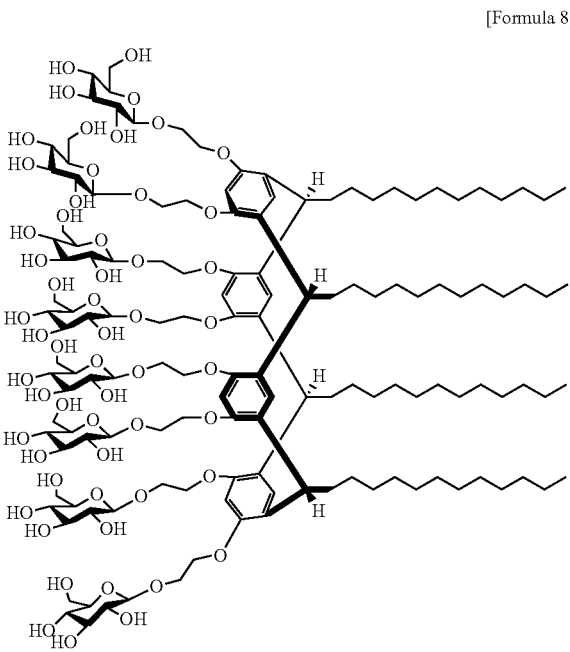

In another embodiment of the present invention, a compound represented by Formula 2, wherein $R^1$ to $R^4$ are $C_2$ alkyl groups; $X^1$ to $X^4$ are maltoses; and $m^1$ to $m^4$ are 0, is referred to as "RMA-$C_3$". Accordingly, the compound may be a compound represented by the following Formula 9:

[Formula 9]

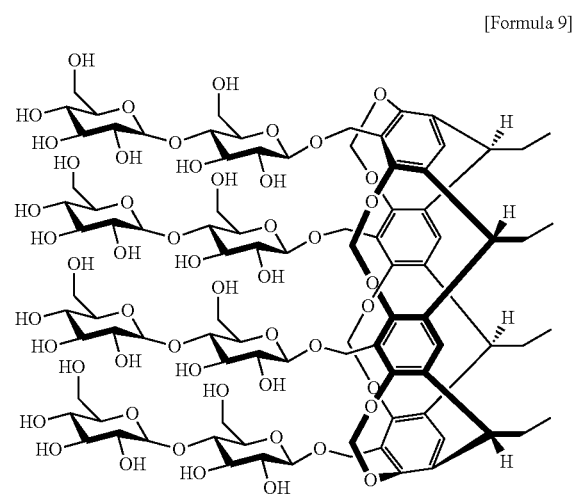

In another embodiment of the present invention, a compound represented by Formula 2, wherein $R^1$ to $R^4$ are $C_3$ alkyl groups; $X^1$ to $X^4$ are maltoses; and $m^1$ to $m^4$ are 0, is referred to as "RMA-C4". Accordingly, the compound may be a compound represented by the following Formula 10:

[Formula 10]

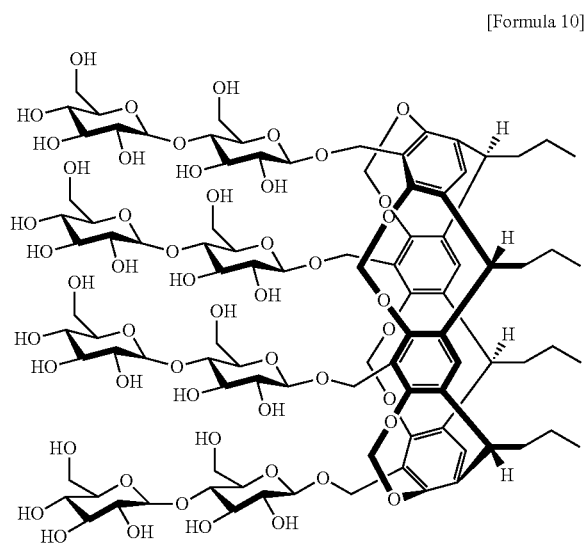

In another embodiment of the present invention, a compound represented by Formula 2, wherein $R^1$ to $R^4$ are $C_4$ alkyl groups; $X^1$ to $X^4$ are maltoses; and $m^1$ to $m^4$ are 0, is referred to as "RMA-C5". Accordingly, the compound may be a compound represented by the following Formula 11:

[Formula 11]

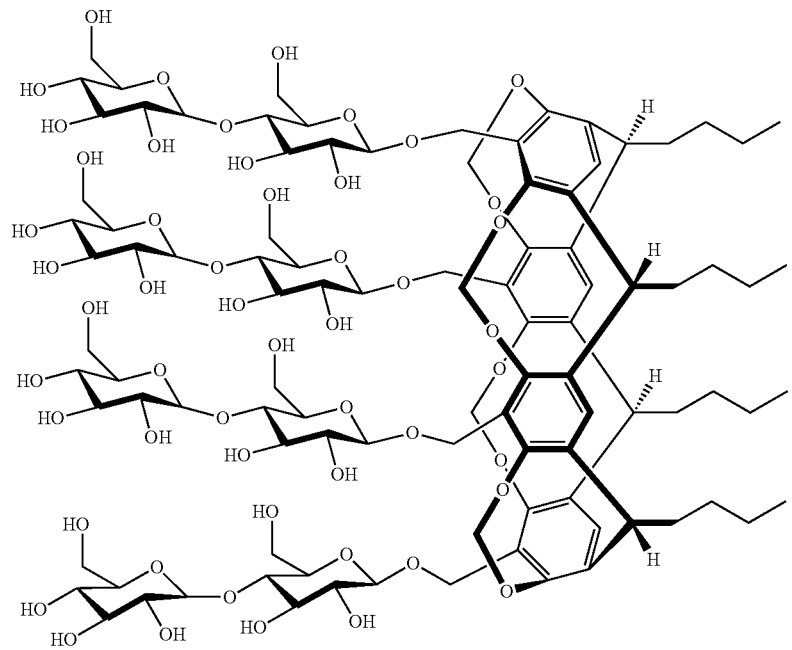

In another embodiment of the present invention, a compound represented by Formula 2, wherein $R^1$ to $R^4$ are $C_2$ alkyl groups; $X^1$ to $X^4$ are maltoses; and $m^1$ to $m^4$ are 1, is referred to as "RMA-C3E". Accordingly, the compound may be a compound represented by the following Formula 12:

[Formula 12]

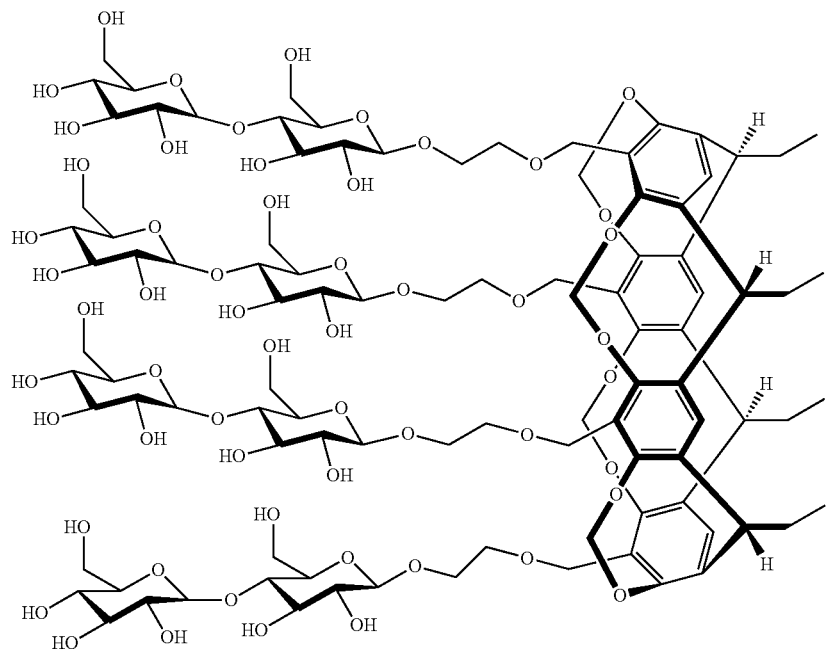

In another embodiment of the present invention, a compound represented by Formula 2, wherein $R^1$ to $R^4$ are $C_3$ alkyl groups; $X^1$ to $X^4$ are maltoses; and $m^1$ to $m^4$ are 1, is referred to as "RMA-C4E". Accordingly, the compound may be a compound represented by the following Formula 13:

[Formula 13]

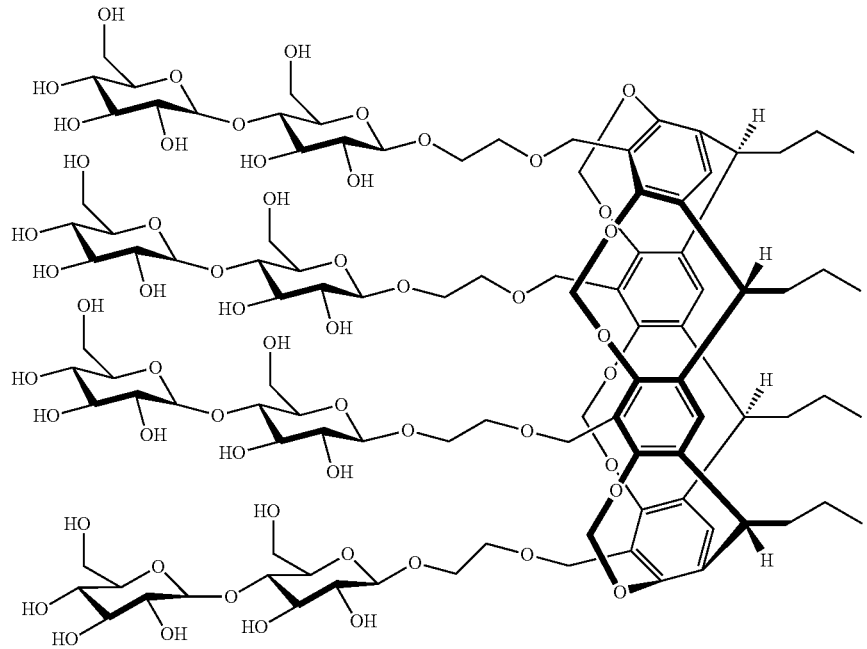

In another embodiment of the present invention, a compound represented by Formula 2, wherein $R^1$ to $R^4$ are $C_4$ alkyl groups; $X^1$ to $X^4$ are maltoses; and $m^1$ to $m^4$ are 1, is referred to as "RMA-C5E". Accordingly, the compound may be a compound represented by the following Formula 14:

[Formula 14]

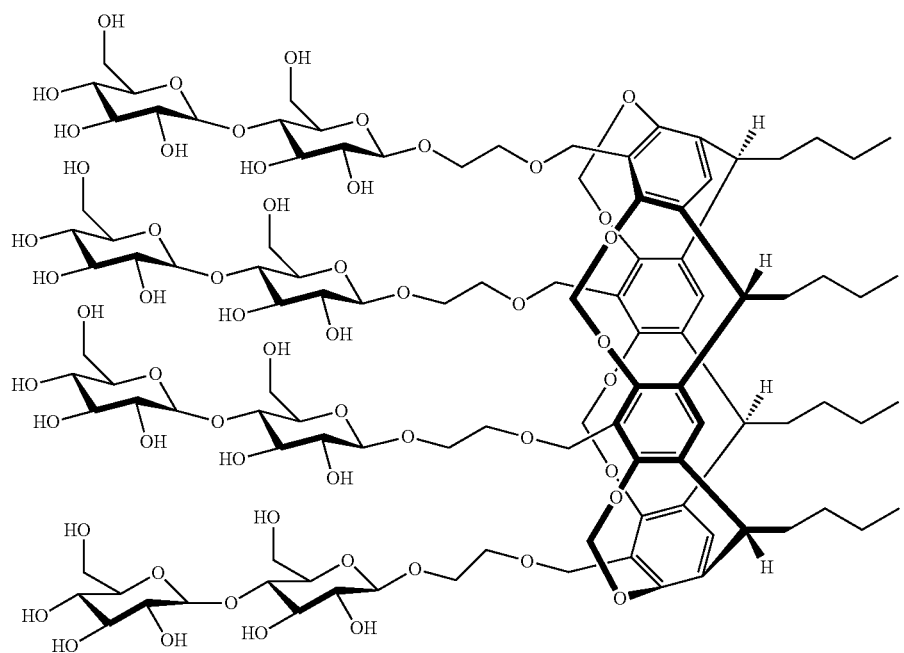

The compound according to an embodiment of the present invention may be an amphipathic molecule for extracting, solubilizing, stabilizing, crystallizing, or analyzing a membrane protein, but the present invention is not limited thereto.

Specifically, the extraction may be performed by extracting a membrane protein from a cell membrane.

The term "amphipathic molecule" used herein refers to a molecule which includes both hydrophobic and hydrophilic groups and thus has affinity for two types of substances, i.e., polar and nonpolar solvents. Phospholipid molecules present in a surfactant or a cell membrane are amphipathic, i.e., have hydrophilic groups at one end thereof and hydrophobic groups at the other end, and form micelles or liposomes in an aqueous solution. Since the hydrophilic groups have polarity and nonpolar groups coexist with the hydrophilic groups, the amphipathic molecules tend not to be readily soluble in an aqueous solution. However, when the concentration of the molecules is equal to or greater than a critical micelle concentration (CMC), the hydrophobic groups are gathered in the interiors of the molecules by hydrophobic interactions and thus spherical or elliptical micelles, at surfaces of which hydrophilic groups are exposed, are generated, thereby the solubility of the molecules in water significantly increases.

A method of measuring the CMC is not particularly limited and may be any method generally known in the art. For example, the CMC may be measured according to a fluorescence staining method using diphenylhexatriene (DPH).

The compound according to an embodiment of the present invention may have a critical micelle concentration (CMC) of 0.0001 to 1 mM, particularly 0.0001 to 0.1 mM, more particularly 0.001 to 0.1 mM, and even more particularly 0.001 to 0.05 mM in an aqueous solution, and may have, for example, a CMC of 0.005 to 0.05 mM, but the present invention is not limited thereto.

Compared to DDM which is conventionally and mainly used in research on membrane proteins and has a CMC of 0.17 mM, RGAs or RMAs according to the embodiment of the present invention have very low CMC values. Accordingly, since RGAs or RMAs easily form micelles even at low concentrations, a small amount of RGAs or RMAs may be used to effectively study and analyze membrane proteins. Therefore, RGAs or RMAs are more advantageous than DDM in terms of applications.

In accordance with another aspect of the present invention, there is provided a composition for extracting, solubilizing, stabilizing, crystallizing, or analyzing a membrane protein, which includes the above-described compound.

Specifically, the extraction may be performed by extracting a membrane protein from a cell membrane.

The composition may be a micelle, liposome, emulsion, or nanoparticle formulation, but the present invention is not limited thereto.

The micelle may have a radius of 2.0 nm to 20 nm, particularly 2.0 nm to 10.0 nm, and may have, for example, a radius of 2.8 nm to 7.5 nm, but the present invention is not limited thereto.

A method of measuring the radius of a micelle is not particularly limited and may be any method generally known in the art. For example, the radius may be measured by a dynamic light scattering (DLS) experiment.

The micelle, the liposome, the emulsion, or the nanoparticle may be hydrophobically bonded to a membrane protein in the interior thereof. That is, the micelle, liposome, emulsion, or nanoparticle may extract and envelop a membrane protein present inside a cell membrane. Accordingly, it is possible to extract, solubilize, stabilize, crystallize, or analyze a membrane protein using the micelle.

The composition may further include a buffer, etc. which may help to extract, solubilize, stabilize, crystallize, or analyze a membrane protein.

In accordance with still another aspect of the present invention, there is provided a method of preparing a compound represented by the following Formula 1, which includes the following steps 1) to 3):

1) introducing an alkyl group by acid-catalyzed condensation of four 1,3-bis(2-hydroxyethoxy)benzene compounds;
2) introducing a protective group-attached saccharide by glycosylating the product of step 1); and
3) de-protecting the product of step 2):

[Formula 1]

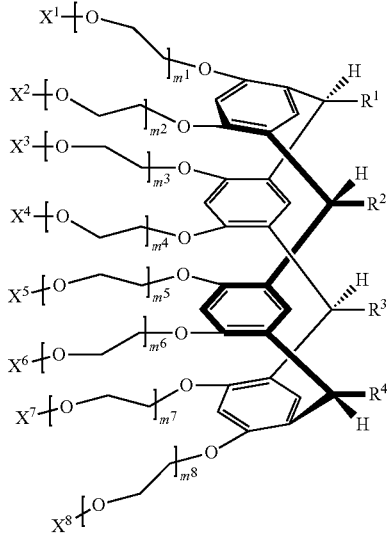

In Formula 1, $R^1$ to $R^4$ may be each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^8$ may be saccharides; and $m^1$ to $m^8$ may be 0, 1, or 2.

Specifically, $R^1$ to $R^4$ may be each independently a substituted or unsubstituted $C_3$-$C_{30}$ alkyl group; and $X^1$ to $X^8$ may be glucoses.

A compound synthesized according to the above preparation method may be a compound represented by one of Formulas 3 to 8 according to an embodiment of the present invention, but the present invention is not limited thereto.

In this embodiment, a compound may be synthesized using a simple method constituted of three synthesis steps, and thus a compound used in research on membrane proteins may be mass-produced.

In accordance with yet another aspect of the present invention, there is provided a method of preparing a compound represented by the following Formula 2, which includes the following steps 1) to 6):

1) introducing an alkyl group by acid-catalyzed condensation of four methyl resorcinol compounds;
2) subjecting the product of step 1) to a methylene bridging reaction using bromochloromethane;

3) brominating a benzylic position in the product of step 2);

4) hydrolyzing or causing the product of step 3) to have ethylene glycol linkages;

5) introducing a protective group-attached saccharide by glycosylating the product of step 4); and 6) de-protecting the product of step 5):

[Formula 2]

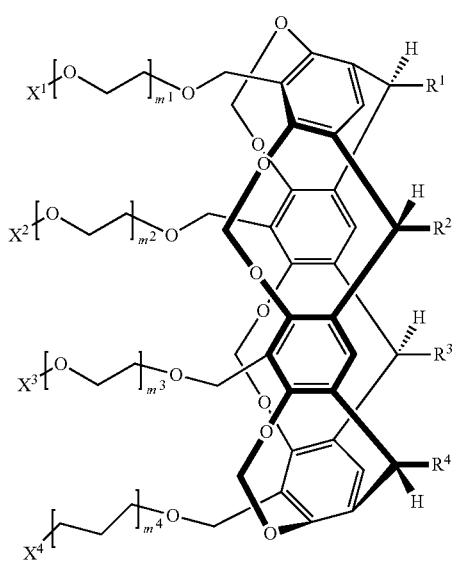

In Formula 2, $R^1$ to $R^4$ may be each independently a substituted or unsubstituted $C_2$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^4$ may be saccharides; and $m^1$ to $m^4$ may be 0, 1, or 2.

Specifically, $R^1$ to $R^4$ may be each independently a substituted or unsubstituted $C_2$-$C_{30}$ alkyl group; $X^1$ to $X^4$ may be maltoses; and $m^1$ to $m^4$ are 1.

A compound synthesized according to the above preparation method may be a compound represented by one of Formulas 9 to 14 according to an embodiment of the present invention, but the present invention is not limited thereto.

In accordance with yet another aspect of the present invention, there is provided a method of extracting, solubilizing, stabilizing, crystallizing, or analyzing a membrane protein. Specifically, there is provided a method of extracting, solubilizing, stabilizing, crystallizing, or analyzing a membrane protein, which includes treating a membrane protein with a compound represented by the following Formula 1 or Formula 2 in an aqueous solution:

[Formula 1]

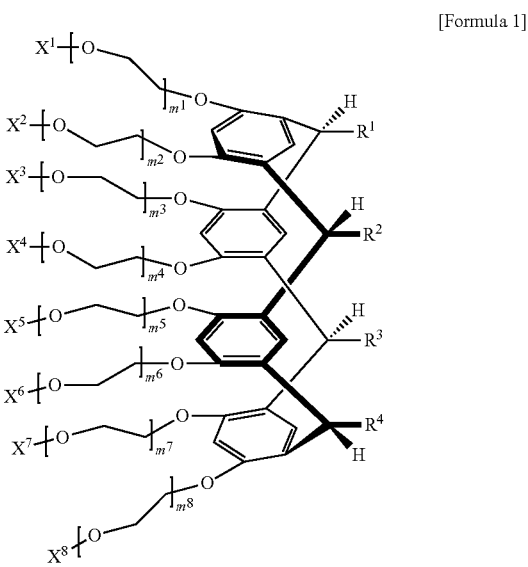

In Formula 1, $R^1$ to $R^4$ may be each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^8$ may be saccharides; and $m^1$ to $m^8$ may be 0, 1, or 2.

[Formula 2]

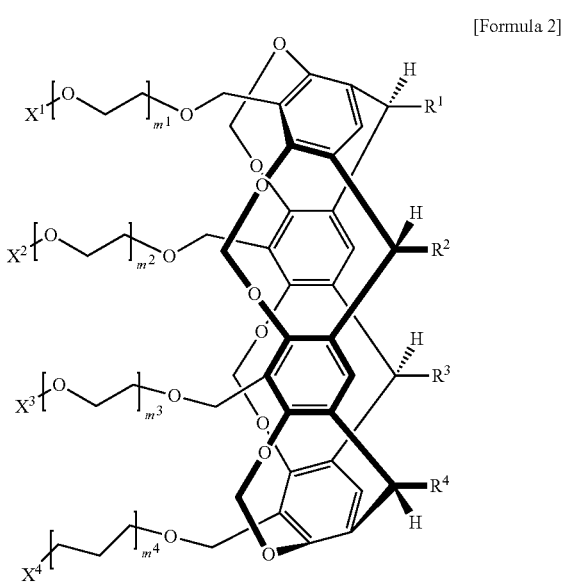

In Formula 2, $R^1$ to $R^4$ may be each independently a substituted or unsubstituted $C_2$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^4$ may be saccharides; and $m^1$ to $m^4$ may be 0, 1, or 2.

Specifically, $R^1$ to $R^4$ may be each independently a substituted or unsubstituted alkyl group described hereinabove; $X^1$ to $X^8$ may be glucoses or maltoses; and $m^1$ to $m^8$ may be 0, 1, or 2.

The compound may be a compound represented by one of Formulas 3 to 14 according to an embodiment of the present invention, but the present invention is not limited thereto.

Specifically, the extraction may be performed by extracting a membrane protein from a cell membrane.

The term "membrane protein" used herein is a generic term for proteins or glycoproteins which ingress into a lipid bilayer of a cell membrane. Membrane proteins are present in various states, i.e., membrane proteins may pass through entire layers of a cell membrane, be located on a surface layer, or adhere to a cell membrane. Examples of membrane proteins include enzymes, peptide hormones, receptors such as local hormones, etc., receptor carriers such as saccharides, etc., ion channels, cell membrane antigens, etc., but the present invention is not limited thereto.

The membrane protein may be any protein or glycoprotein which ingresses into a lipid bilayer of a cell membrane. Specifically, the membrane protein may be a uric acid-xanthine/$H^+$ symporter (UapA), a leucine transporter (LeuT), a human $\beta_2$ adrenergic receptor ($\beta_2$AR), a melibiose permease (MelB), or a combination of two or more thereof, but the present invention is not limited thereto.

The term "extraction of a membrane protein" used herein refers to separating a membrane protein from a cell membrane.

The term "solubilization of a membrane protein" used herein refers to dissolving a membrane protein, which does not dissolve in water, in a micelle in an aqueous solution.

The term "stabilization of a membrane protein" used herein refers to stably preserving a tertiary or quaternary structure of a membrane protein such that the structure and function of the membrane protein are not changed.

The term "crystallization of a membrane protein" used herein refers to forming a crystal of a membrane protein in a solution.

The term "analysis of a membrane protein" used herein refers to analyzing the structure or function of a membrane protein. In this embodiment, the analysis of a membrane protein may be performed by any known method, and, for example, the structures of a membrane protein may be analyzed using an electron microscope or nuclear magnetic resonance (NMR), but the present invention is not limited thereto.

By using the resorcinarene-based amphipathic compounds according to the embodiments of the present invention, a membrane protein can be stably stored in an aqueous solution for a long period, compared to the cases in which existing compounds are used. Accordingly, the resorcinarene-based amphipathic compounds can be utilized to analyze the functions and structures of membrane proteins.

The analysis of membrane protein structure and function is currently one of the most attractive fields of research in biology and chemistry, and thus the compound can be applied to protein structure research closely related to new drug development.

In addition, since a complex formed of the compounds according to the embodiments of the present invention and a membrane protein is small, a high-quality membrane protein crystal can be obtained, thereby crystallization of a membrane protein can be promoted.

In addition, the compounds according to the embodiments of the present invention can be synthesized from easily obtainable starting materials using a simple method, and thus can be mass-produced to perform research on membrane proteins.

BRIEF DESCRIPTION OF THE SEVERAL VIEW OF THE DRAWINGS

FIGS. 4A and 4B are a set of diagrams illustrating size distributions of the micelles formed by RMAs and RGAs.

Figure 7A:
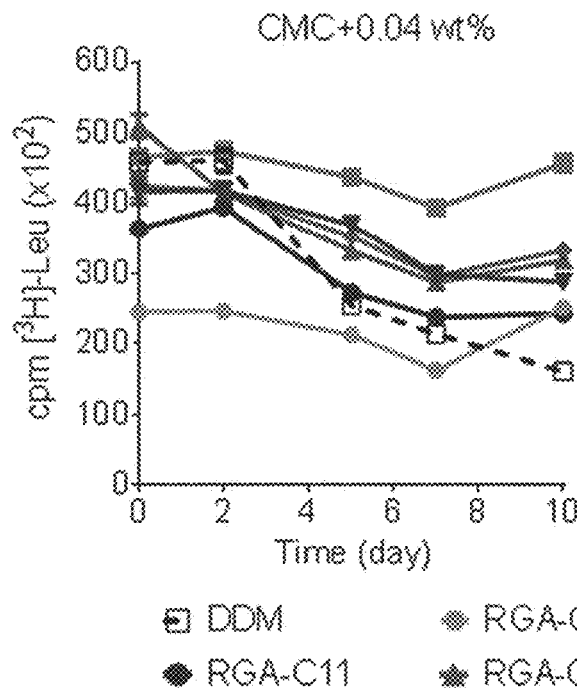
Figure 7B:
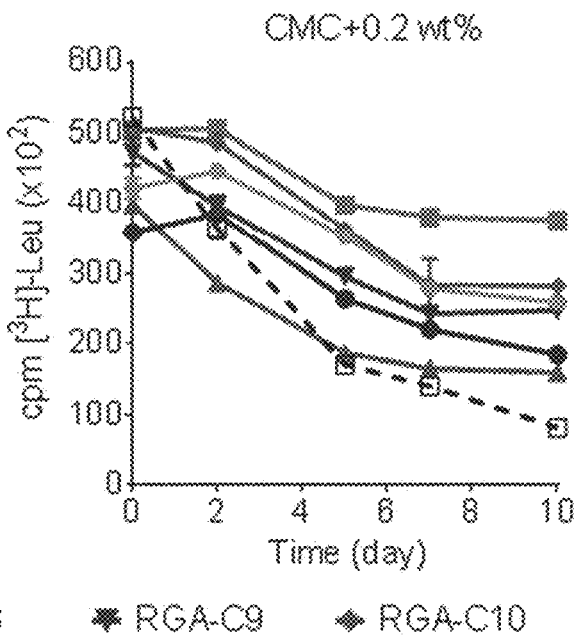

FIGS. 7A and 7B are a set of graphs illustrating a result of measuring the structural stability of a leucine transporter (LeuT) solubilized in RGAs or DDM evaluated at CMC+0.04 wt % (a) or CMC+0.2 wt % (b). Protein stability was determined by measuring the ability of the transporter to bind a radiolabeled ligand ([3H]-Leu) via scintillation proximity assay (SPA). The substrate binding ability of LeuT was measured at regular intervals during 10 days of incubation of the protein at room temperature in the presence of individual amphipathic compounds.

Figure 8A:
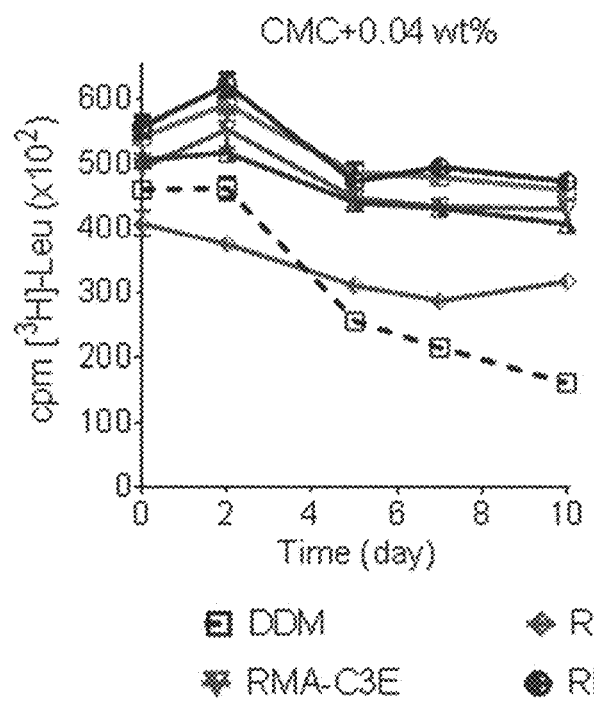
Figure 8B:
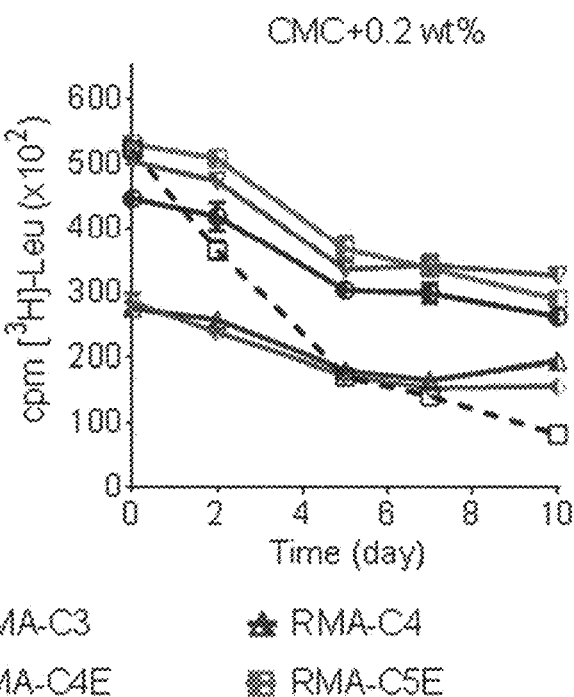

FIGS. 8A and 8B are a set of graphs illustrating a result of measuring the structural stability of a leucine transporter (LeuT) solubilized in RMAs or DDM evaluated at CMC+0.04 wt % (a) or CMC+0.2 wt % (b). Protein stability was determined by measuring the ability of the transporter to bind a radiolabeled ligand ([3H]-Leu) via scintillation proximity assay (SPA). The substrate binding ability of LeuT was measured at regular intervals during 10 days of incubation of the protein at room temperature in the presence of individual amphipathic compounds.

Figure 9A:
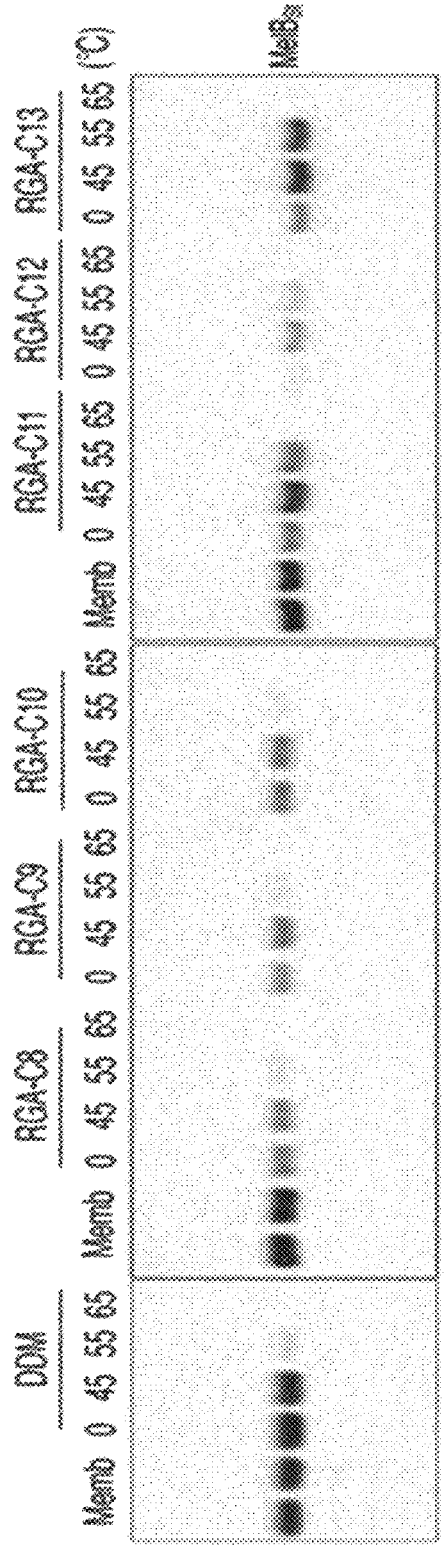
Figure 9B:
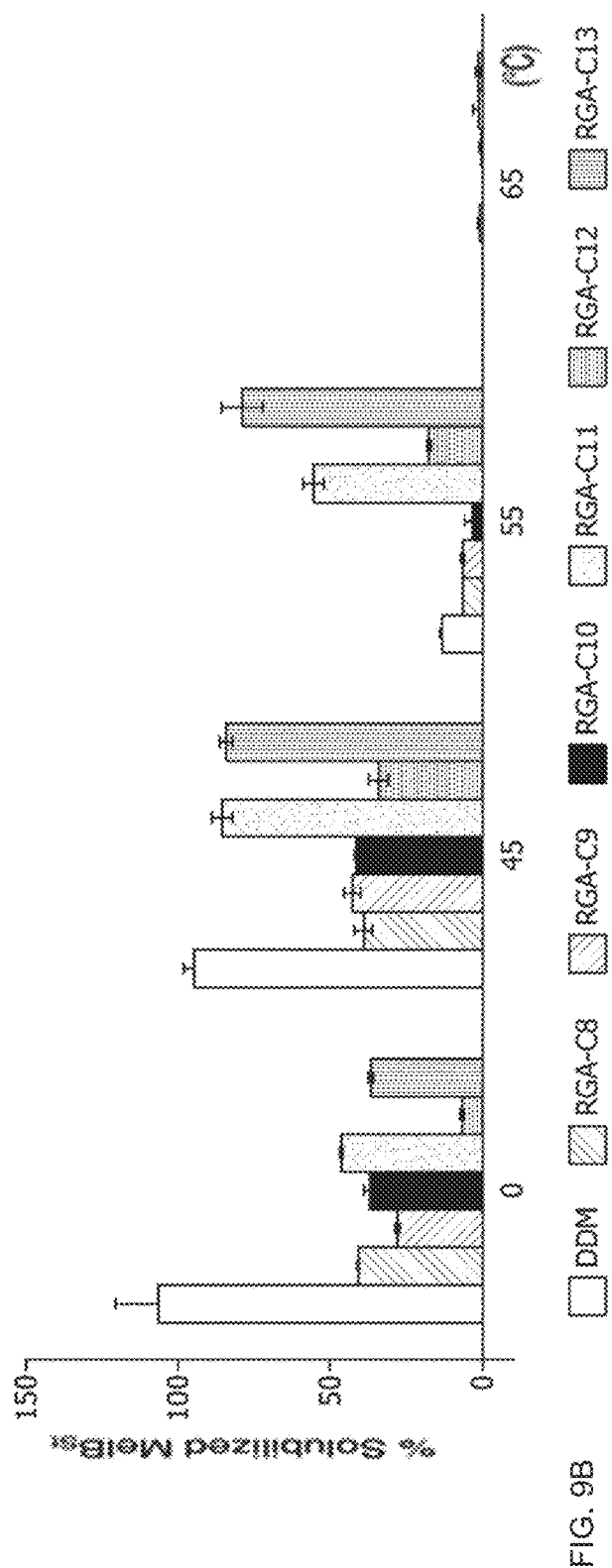

FIGS. 9A and 9B illustrate a result of measuring the amount of a MelB protein dissolved in an aqueous solution after a MelB protein was extracted at four temperatures (0, 45, 55, and 65) using RGAs or DDM at a concentration of 1.5 wt % and then incubated at the same temperatures for 90 minutes:

FIGS. 10A and 10B illustrate a result of measuring the effect of RGAs on the stability of $\beta_2$AR after (a) 0 hour and (b) over time. Protein-ligand binding characteristics were measured via ligand binding assay using [$^3$H]-dihydroalprenolol (DHA), and the measurement was carried out by sampling a protein sample at regular intervals during 2 days of storage at room temperature.

Figure 11:
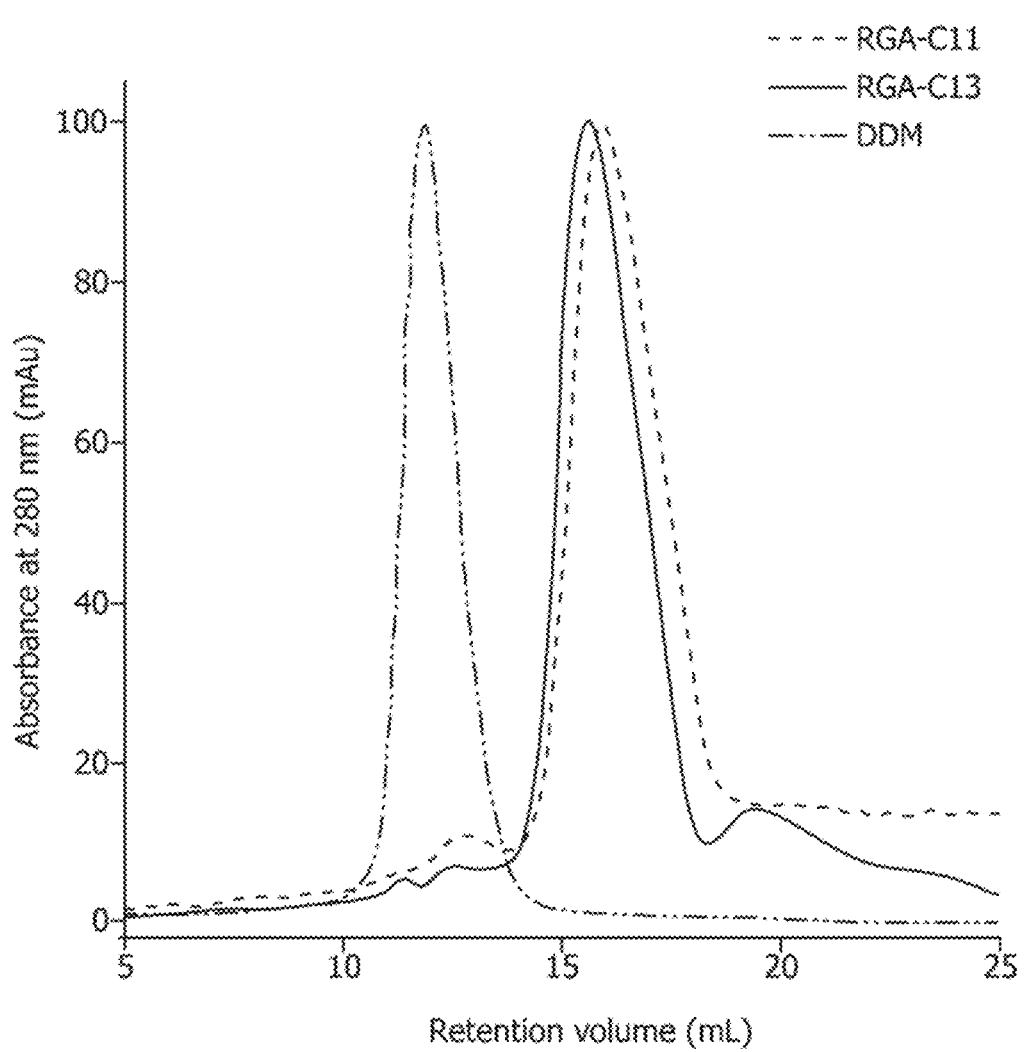

FIG. 11 illustrates a result of evaluating the size characteristic of a (32AR protein-ligand binding complex formed of RGA-C11, RGA-C13, or DDM via a size exclusion chromatography (SEC) test.

FIGS. 12A and 12B illustrate a result of measuring the effect of RMAs on the stability of $\beta_2$AR after (a) 0 hour and (b) over time. Protein-ligand binding characteristics were measured via ligand binding assay using [$^3$H]-dihydroalprenolol (DHA), and the measurement was carried out by sampling a protein sample at regular intervals during 2 days of storage at room temperature.

DESCRIPTION OF SPECIFIC EMBODIMENTS OF THE INVENTION

Hereinafter, the present invention will be described in more detail with reference to the following examples. However, the following examples are provided to exemplify contents of the present invention and the scope of the present invention is not limited to the following examples. It should be understood that examples which can be easily deduced from detailed descriptions and the following examples of the present invention by one of ordinary skill in the art are within the scope of the present invention.

<Example 1> Method of Synthesizing Resorcinarene-Based Maltosides (RMAs)

Figure 1A:
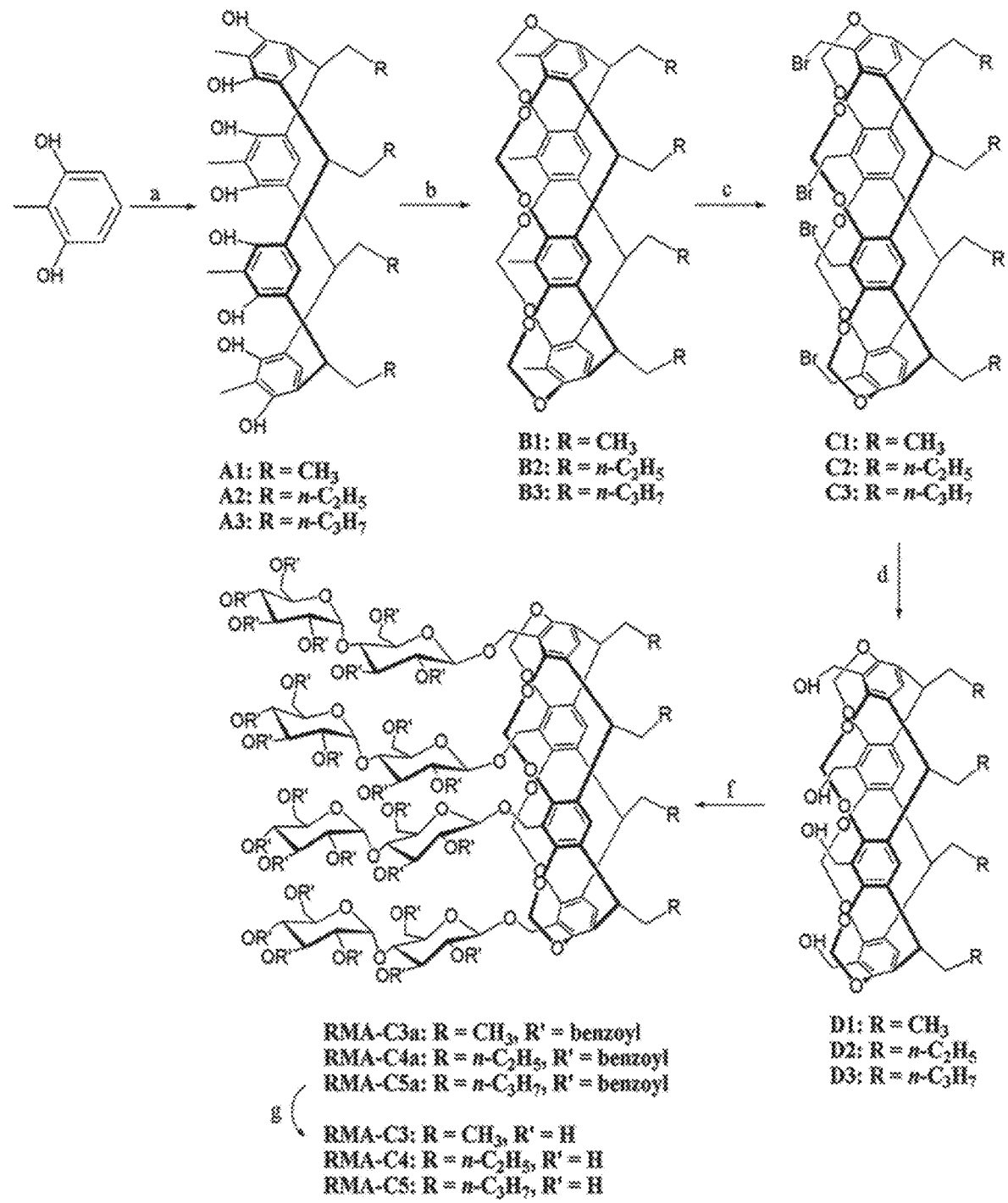
FIGS. 1A and 1B are diagrams illustrating a synthesis scheme of RMAs according to Example 1 of the present invention.
Figure 1B:
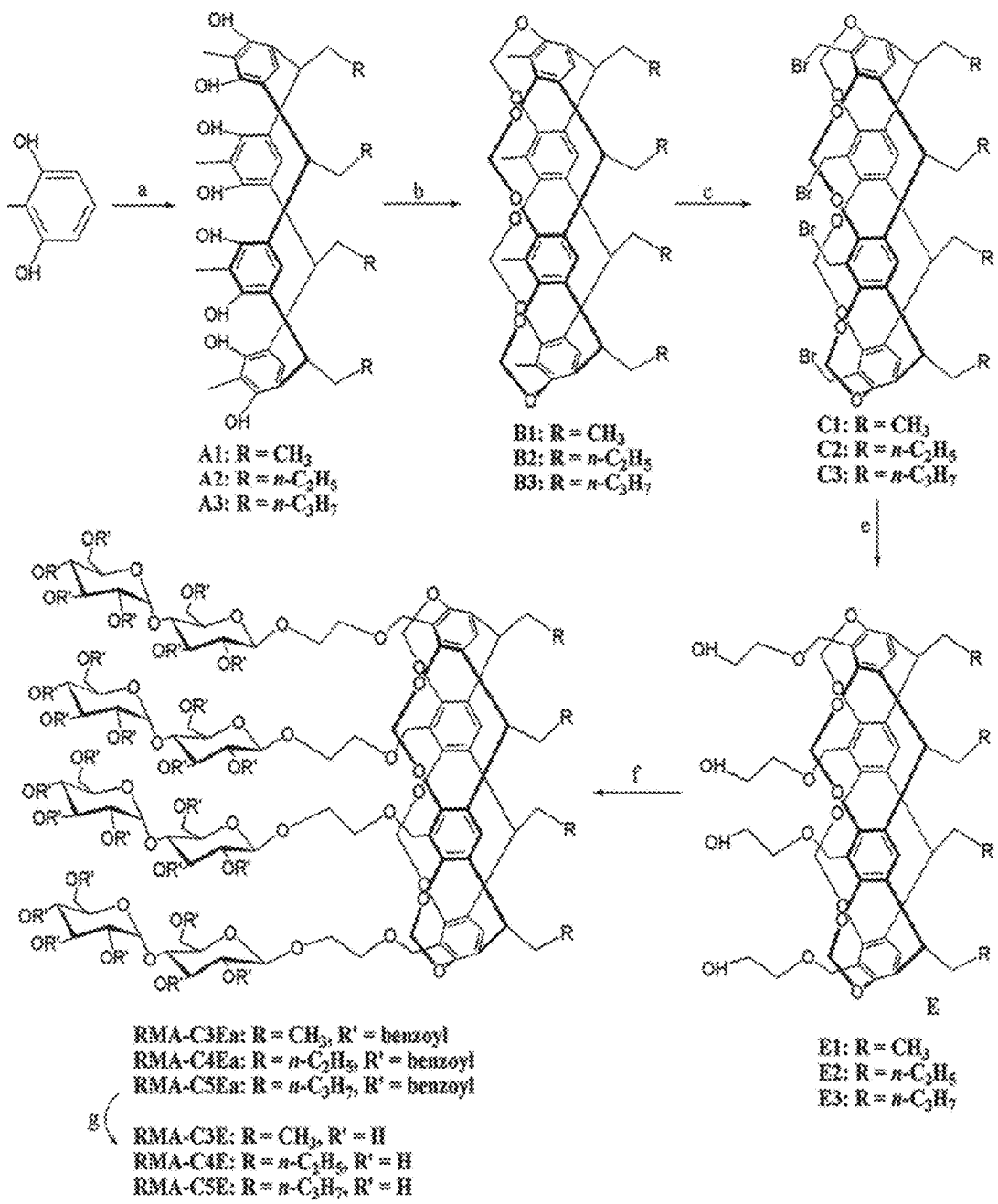
Figure 3:
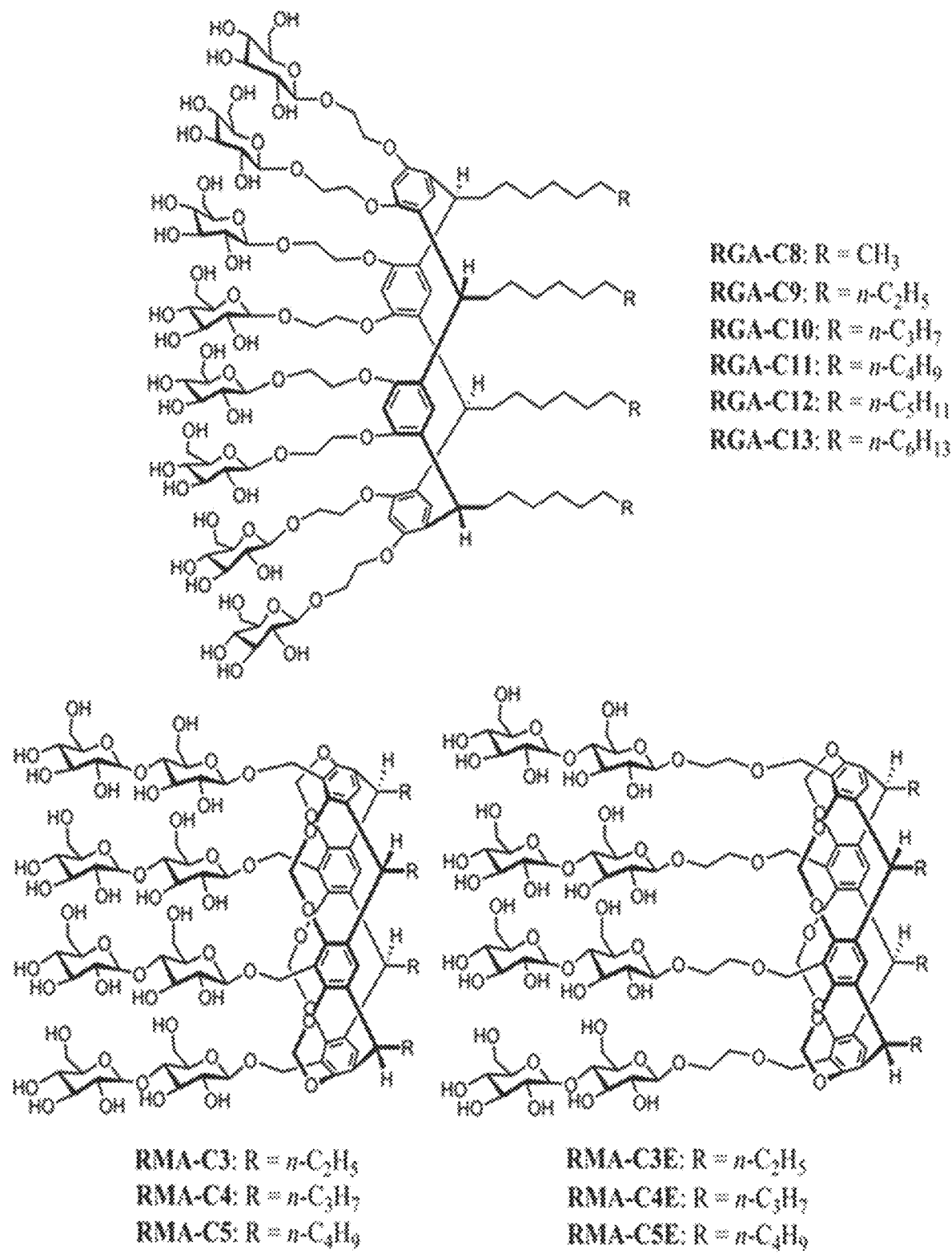
FIG. 3 is a diagram illustrating the chemical structures of RMAs and RGAs according to Examples of the present invention.

A synthesis scheme of RMAs is shown in FIG. 1A and FIG. 1B. Six types of RMAs were synthesized according to the following synthesis methods <1-1> to <1-7>. The synthesized RMAs are shown in FIG. 3.

<1-1> General Procedure for the Synthesis of octol-resorcin[4]arene (Step a of FIG. 1A and FIG. 1B)

Methyl resorcinol (1.0 g, 0.0081 mol) was dissolved in a mixed solution of ethanol (6.27 mL) and 37% HCl (1.51 mL). To the resultant solution, an aldehyde (0.0081 mol) was added at 0° C. over 15 minutes. The reaction mixture was warmed at room temperature, then transferred to a preheated oil bath, and stored at 80° C. for 16 hours while stirring. After completion of the reaction (as detected by TLC), the reaction mixture was added to distilled water. An organic layer was extracted using ethyl acetate and washed twice with water and brine. The organic layer was dried with anhydrous $Na_2SO_4$, and a solvent was removed using a rotary evaporator. The residue was purified by column chromatography, thereby obtaining compound A as a yellow solid.

<1-2> General Procedure for the Synthesis of Tetramethylcavitand (Step b of FIG. 1A and FIG. 1B)

$K_2CO_3$ (88 mmol) was added to a mixed solution (0.55 mmol) of dry DMF and compound A in a sealed tube. To the mixture, bromochloromethane (88 mmol) was added at room temperature, and the resultant mixture was stirred for 30 minutes and then transferred to an oil bath preheated at 80° C. The reaction mixture was stirred at 80° C. for 24 hours. After completion of the reaction (as detected by TLC), ice water was added to the reaction mixture. An organic layer was extracted using ethyl acetate and washed twice with water and brine. The organic layer was dried with anhydrous $Na_2SO_4$, and a solvent was removed using a rotary evaporator. The residue was purified by column chromatography, thereby obtaining compound B as a white solid.

<1-3> General Procedure for the Synthesis of tetrakis(bromomethyl)cavitand (Step c of FIG. 1A and FIG. 1B)

NBS (30 mmol) was added to a solution in which compound B (1.1 mmol) and AIBN (0.6 mmol) were stirred in 10 mL of degassed benzene. The resultant solution was stirred for 30 minutes and transferred to an oil bath preheated at 80° C. The reaction mixture was stirred at 80° C. for 24 hours. After completion of the reaction (as detected by TLC), a solid precipitate (succinimide) was filtered, and benzene was evaporated using a rotary evaporator. The reaction mixture was purified by column chromatography, thereby obtaining compound C as a white crystal solid.

<1-4> General Procedure for the Synthesis of tetrakis(hydroxymethyl)cavitand (Step d of FIG. 1A)

$K_2CO_3$ (2.2 mmol) was added to a mixed solution of 40 mL of acetone and water (9:1) and compound C in a sealed tube, and the sealed tube was immersed in an oil bath preheated at 80° C. The reaction mixture was stirred at 80° C. for 24 hours. After completion of the reaction (as detected by TLC), acetone was evaporated. The residue was purified by column chromatography, thereby obtaining compound D as a white solid.

<1-5> General Procedure for the Synthesis of tetrakis(hydroxyethoxymethyl)cavitand (Step e of FIG. 1B)

NaH was dissolved in dry DMF while stirring, and compound D (0.8 mmol) was added to the stirred suspension. To the resultant solution, ethylene glycol was added, and the mixture was continuously stirred at room temperature for 30 minutes. The reaction mixture was transferred to an oil bath preheated at 80° C. and continuously stirred for 24 hours. After completion of the reaction (as detected by TLC), the reaction mixture was extracted using ethyl acetate and washed with water (2×30 mL) and brine. An organic layer was dried with anhydrous $Na_2SO_4$ and concentrated using a rotary evaporator. The residue was purified by column chromatography, thereby obtaining compound E as a white solid.

<1-6> General Procedure for Glycosylation Reaction (Step f of FIG. 1A and FIG. 1B)

Glycosylation was carried out according to the synthesis method (*Nat. Methods* 2010, 7. 1003.) written by P. S. Chae et al. To a solution in which an alcohol derivative (compound D or E) was stirred in $CH_2Cl_2$ (15 mL), 2,4,6-collidine (maltose (3.0 equiv.) or glucose (6.0 equiv.)) was added. AgOTf (maltose (5.0 equiv.) or glucose (10.0 equiv.)) was added to the resultant mixture at 0° C. After stirring for 10 minutes, a solution of perbenzoylated maltosylbromide (5.0 equiv. or 10.0 equiv.) dissolved in $CH_2Cl_2$ was slowly added thereto. The reaction was carried out for 30 minutes while stirring. After completion of the reaction (as detected by TLC), pyridine was added to the reaction mixture, and the mixture was diluted with $CH_2Cl_2$ (20 mL) before being filtered over Celite. A filtrate was washed with a 1 M aqueous $Na_2S_2O_3$ solution (40 mL), a 0.1 M aqueous HCl solution (40 mL), and brine (3×40 mL). Then, an organic layer was dried with anhydrous $Na_2SO_4$, and a solvent was removed using a rotary evaporator. The residue was purified by silica gel column chromatography (EtOAc/hexane), thereby obtaining a glycosylated compound as a glassy solid.

<1-7> General Procedure for De-Protection Reaction (Step g of FIG. 1A and FIG. 1B)

De-protection was carried out according to the synthesis method (*Nat. Methods* 2010, 7. 1003.) written by P. S. Chae et al. De-O-benzoylation was carried out under Zemplén's conditions. An O-protected compound was dissolved in anhydrous $CH_2Cl_2$ and then MeOH was slowly added thereto until precipitation continuously appeared. To the reaction mixture, a methanolic solution of 0.5 M NaOMe was added such that the final concentration was 0.05 M. The reaction mixture was stirred at room temperature for 6 hours. After completion of the reaction, the reaction mixture was neutralized with an Amberlite IR-120 ($H^+$ form) resin. The resin was removed by filtration, a filtrate was washed with MeOH, and a solvent was removed from the filtrate in vacuo. The residue was recrystallized using $CH_2Cl_2$/MeOH/diethyl ether, thereby obtaining a purer de-O-benzolyated compound as a white solid. The compounds thus obtained are RMAs which are the compounds of the present invention.

<Preparation Example 1> Synthesis of RMA-C3

<1-1> Synthesis of Compound A1

According to the general procedure for the synthesis of octol-resorcin[4]arene in Example 1-1, compound A1 was synthesized in 80% yield.

<1-2> Synthesis of Compound B1

According to the general procedure for the synthesis of tetramethylcavitand in Example 1-2, compound B1 was synthesized in 80% yield.

<1-3> Synthesis of Compound C1

According to the general procedure for the synthesis of tetrakis(bromomethyl)cavitand in Example 1-3, compound C1 was synthesized in 81% yield.

<1-4> Synthesis of Compound D1

According to the general procedure for the synthesis of tetrakis(hydroxymethyl)cavitand in Example 1-4, compound D1 was synthesized in 70% yield.

<1-5> Synthesis of RMA-C3a

According to the general procedure for a glycosylation reaction in Example 1-6, RMA-C3a was synthesized in 35% yield. $^1$H NMR (400 MHz, $CDCl_3$): δ 8.07 (d, J=7.2 Hz, 8H), 8.01 (d, J=7.1 Hz, 8H), 7.91-7.85 (m 12H), 7.75-7.71 (m, 20H), 7.60 (d, J=7.2 Hz, 8H), 7.59-7.48 (m, 28H), 7.47-7.31 (m, 32H), 7.29-7.15 (m, 20H), 6.94 (s, 4H), 6.09 (t, J=10.0 Hz, 4H), 5.81-5.60 (m, 16H), 5.42 (d, J=7.2 Hz, 2H), 5.31-5.19 (m, 8H), 4.82 (d, J=10.2 Hz, 2H), 4.71-4.59 (m, 6H), 4.51-4.31 (m, 20H), 4.23-4.18 (m, 4H), 4.15-3.91 (m, 6H), 2.23-2.17 (m, 8H), 0.83 (t, J=7.1 Hz, 12H); $^{13}$C NMR (100 MHz, $CDCl_3$): δ 171.2, 166.1, 165.8, 165.6, 165.5, 165.2, 165.1, 154.2, 154.1, 137.7, 137.5, 133.3, 133.2, 133.1, 130.0, 129.9, 129.8, 129.6, 129.3, 129.2, 129.0, 128.8, 128.6, 128.4, 128.2, 128.1, 122.7, 120.7, 99.9, 99.3, 77.4, 75.4, 73.2, 73.1, 72.0, 71.0, 70.0, 69.2, 69.0, 63.5, 62.4, 61.3, 60.4, 53.5, 38.5, 22.9, 21.1, 14.2, 12.3.

<1-6> Synthesis of RMA-C3

According to the general procedure for a de-protection reaction in Example 1-7, RMA-C3 was synthesized in 85% yield. $^1$H NMR (400 MHz, $CD_3OD$): δ 7.32 (s, 4H), 5.89 (d, J=7.8 Hz, 4H), 5.20 (s, 5H), 4.72-4.57 (m, 10H), 4.55-4.32 (m, 12H), 3.98-3.81 (m, 16H), 3.79-3.68 (m, 12H), 3.67-3.58 (m, 16H), 3.57-5.43 (m, 8H), 3.29-3.19 (m, 4H), 2.45-2.29 (m, 8H), 0.99 (t, J=6.8 Hz, 12H); $^{13}$C NMR (100 MHz, $CD_3OD$): δ 155.7, 139.4, 103.0, 81.4 77.8, 75.1, 74.9, 74.2, 71.6, 64.1, 62.8, 62.4, 33.1, 22.2, 14.5. MS (MALDI-TOF): calcd. for $C_{92}H_{128}O_{52}$ $[M+Na]^+$ 2087.7264, found 2087.7190.

<Preparation Example 2> Synthesis of Compound RMA-C4

<2-1> Synthesis of Compound A2

According to the general procedure for the synthesis of octol-resorcin[4]arene in Example 1-1, compound A2 was synthesized in 81% yield.

<2-2> Synthesis of Compound B2

According to the general procedure for the synthesis of tetramethylcavitand in Example 1-2, compound B2 was synthesized in 82% yield.

<2-3> Synthesis of Compound C2

According to the general procedure for the synthesis of tetrakis(bromomethyl)cavitand in Example 1-3, compound C2 was synthesized in 83% yield.

<2-4> Synthesis of Compound D2

According to the general procedure for the synthesis of tetrakis(hydroxymethyl)cavitand in Example 1-4, compound D2 was synthesized in 72% yield.

<2-5> Synthesis of RMA-C4a

According to the general procedure for a glycosylation reaction in Example 1-6, RMA-C4a was synthesized in 35% yield. $^1$H NMR (400 MHz, $CDCl_3$): δ 8.06 (d, J=7.2 Hz, 8H), 8.01 (d, J=7.1 Hz, 8H), 7.89-7.79 (m 12H), 7.74-7.69 (m, 20H), 7.60 (d, J=7.2 Hz, 8H), 7.58-7.48 (m, 28H), 7.47-7.30 (m, 32H), 7.30-7.16 (m, 20H), 6.94 (s, 4H), 6.10 (t, J=10.0 Hz, 4H), 5.80-5.61 (m, 12H), 5.42 (d, J=7.2 Hz, 2H), 5.31-5.19 (m, 8H), 4.82 (d, J=10.2 Hz, 2H), 4.71-4.59 (m, 6H), 4.50-4.29 (m, 20H), 4.25-4.19 (m, 4H), 4.15-3.89 (m, 6H), 2.20-2.16 (m, 8H), 1.65 (s, 4H), 1.31-1.17 (m, 8H), 0.92 (t, J=7.1 Hz, 12H); $^{13}$C NMR (100 MHz, $CDCl_3$): δ 171.1, 166.2, 165.9, 165.7, 165.6, 165.3, 165.2, 154.3, 154.1, 137.9, 137.8, 133.7, 133.5, 133.3, 133.2, 130.1, 130.0, 129.9, 129.7, 129.4, 129.2, 129.1, 128.9, 128.7, 128.5, 128.3, 128.2, 122.7, 120.9, 100.0, 99.4, 96.6, 73.9, 73.3, 72.1, 71.1, 70.1, 69.3, 69.1, 66.0, 63.6, 62.5, 60.6, 36.5, 32.0, 21.2, 21.1, 15.4, 14.4, 14.3.

<2-6> Synthesis of RMA-C4

According to the general procedure for a de-protection reaction in Example 1-7, RMA-C4 was synthesized in 85% yield. $^1$H NMR (400 MHz, $(CD_3)_2SO$): δ 7.62 (s, 4H), 5.89 (d, J=7.0 Hz, 4H), 5.56-5.41 (m, 8H), 5.01-4.81 (m, 16H), 4.71-4.47 (m, 8H), 4.37-4.21 (m, 12H), 3.82-3.68 (m, 4H), 3.67-3.54 (m, 8H), 3.52-5.43 (m, 8H), 3.32-3.19 (m, 12H), 3.16-3.06 (m, 4H), 2.96-2.88 (m, 4H), 2.42-2.29 (m, 8H), 1.36-1.27 (m, 8H), 0.99 (t, J=7.4 Hz, 12H); $^{13}$C NMR (100 MHz, $(CD_3)_2SO$): δ 153.7, 153.4, 137.7, 123.8, 102.4, 100.8, 79.6, 76.4, 75.3, 73.4, 73.3, 72.7, 72.4, 69.9, 60.8, 48.6, 39.9, 31.2, 20.6, 13.9; MS (MALDI-TOF): calcd. for $C_{96}H_{136}O_{52}$ [M+Na]$^+$ 2143.7890, found 2143.7869.

<Preparation Example 3> Synthesis of RMA-C5

<3-1> Synthesis of Compound A3

According to the general procedure for the synthesis of octol-resorcin[4]arene in Example 1-1, compound A3 was synthesized in 84% yield.

<3-2> Synthesis of Compound B3

According to the general procedure for the synthesis of tetramethylcavitand in Example 1-2, compound B3 was synthesized in 84% yield.

<3-3> Synthesis of Compound C3

According to the general procedure for the synthesis of tetrakis(bromomethyl)cavitand in Example 1-3, compound $C_3$ was synthesized in 85% yield.

<3-4> Synthesis of Compound D3

According to the general procedure for the synthesis of tetrakis(hydroxymethyl)cavitand in Example 1-4, compound D3 was synthesized in 75% yield.

<3-5> Synthesis of RMA-C5a

According to the general procedure for a glycosylation reaction in Example 1-6, RMA-C5a was synthesized in 38% yield. $^1$H NMR (400 MHz, CDCl$_3$): δ 8.07 (d, J=7.2 Hz, 8H), 7.97 (d, J=7.1 Hz, 8H), 7.90-7.79 (m, 8H), 7.78-7.68 (m, 20H), 7.61 (d, J=7.2 Hz, 8H), 7.58-7.49 (m, 28H), 7.48-7.30 (m, 32H), 7.29-7.16 (m, 20H), 6.95 (s, 4H), 6.11 (t, J=10.0 Hz, 4H), 5.82-5.59 (m, 12H), 5.41 (d, J=7.2 Hz, 2H), 5.31-5.19 (m, 8H), 4.82 (d, J=10.2 Hz, 2H), 4.76-4.61 (m, 6H), 4.54-4.29 (m, 20H), 4.25-4.19 (m, 4H), 4.12-3.92 (m, 6H), 2.22-1.97 (m, 8H), 1.52-1.15 (m, 16H), 0.92 (t, J=7.1 Hz, 12H); $^{13}$C NMR (100 MHz, CDCl$_3$): δ 166.1, 165.8, 165.6, 165.5, 165.2, 165.1, 154.2, 154.0, 137.8, 137.7, 133.5, 133.4, 133.2, 133.1, 130.0, 129.9, 129.8, 129.6, 129.3, 129.1, 129.0, 128.7, 128.5, 128.4, 128.3, 128.2, 128.1, 122.6, 120.7, 99.9, 99.2, 96.5, 75.4, 73.1, 73.0, 72.0, 71.0, 69.9, 69.2, 69.0, 63.5, 62.3, 61.2, 60.4, 53.5, 36.7, 30.0, 29.6, 22.9, 14.2.

<3-6> Synthesis of RMA-C5

According to the general procedure for a de-protection reaction in Example 1-7, RMA-C5 was synthesized in 87% yield. $^1$H NMR (400 MHz, (CD$_3$)$_2$SO): δ 7.60 (s, 4H), 5.89 (d, J=6.9 Hz, 4H), 5.54-5.41 (m, 8H), 5.10-4.91 (m, 16H), 4.67-4.43 (m, 8H), 4.37-4.19 (m, 12H), 3.82-3.68 (m, 4H), 3.67-3.54 (m, 8H), 3.50-5.41 (m, 8H), 3.31-3.19 (m, 12H), 3.10-3.01 (m, 4H), 2.96-2.89 (m, 4H), 2.41-2.22 (m, 8H), 1.56-1.21 (m, 16H), 0.91 (t, J=7.2 Hz, 12H); $^{13}$C NMR (100 MHz, (CD$_3$)$_2$SO): δ 153.6, 153.3, 137.6, 123.7, 102.4, 100.7, 79.5, 76.4, 75.2, 73.3, 73.2, 72.6, 72.4, 69.9, 60.8, 60.6, 39.1, 29.9, 28.9, 22.1, 14.0; MS (MALDI-TOF): calcd. for $C_{100}H_{114}O_{52}$ [M+Na]$^+$ 2199.8516, found 2199.8540.

<Preparation Example 4> Synthesis of RMA-C3E

<4-1> Synthesis of Compound A1

According to the general procedure for the synthesis of octol-resorcin[4]arene in Example 1-1, compound A1 was synthesized in 80% yield.

<4-2> Synthesis of Compound B1

According to the general procedure for the synthesis of tetramethylcavitand in Example 1-2, compound B1 was synthesized in 80% yield.

<4-3> Synthesis of Compound C1

According to the general procedure for the synthesis of tetrakis(bromomethyl)cavitand in Example 1-3, compound C1 was synthesized in 81% yield.

<4-4> Synthesis of Compound E1

According to the general procedure for the synthesis of tetrakis(hydroxyethoxymethyl)cavitand in Example 1-5, compound E1 was synthesized in 62% yield.

<4-5> Synthesis of RMA-C3Ea

According to the general procedure for a glycosylation reaction in Example 1-6, RMA-C3Ea was synthesized in 40% yield. $^1$H NMR (400 MHz, CDCl$_3$): δ 8.07 (d, J=7.2 Hz, 8H), 7.96 (d, J=7.1 Hz, 8H), 7.85-7.59 (m, 32H), 7.56 (d, J=7.2 Hz, 8H), 7.49-7.32 (m, 32H), 7.31-7.20 (m, 28H), 7.19-7.04 (m, 20H), 6.92 (s, 4H), 6.02 (t, J=10.0 Hz, 4H), 5.70-5.49 (m, 14H), 5.31-5.13 (m, 8H), 4.92-4.59 (m, 10H), 4.57-4.41 (m, 6H), 4.40-4.35 (m, 8H), 4.25-4.19 (m, 4H), 4.17-3.90 (m, 6H), 3.88-3.79 (m, 4H), 3.62-3.49 (m, 4H), 3.47-3.30 (m, 4H), 2.19-2.12 (m, 8H), 1.65 (s, 4H), 1.31-1.17 (m, 8H), 0.86 (t, J=7.1 Hz, 12H); $^{13}$C NMR (100 MHz, CDCl$_3$): δ 171.2, 166.3, 165.9, 165.8, 165.5, 165.3, 165.2, 165.1, 154.2, 154.1, 154.0, 153.9, 153.6, 138.0, 137.8, 133.7, 137.4, 137.2, 133.6, 133.5, 133.2, 133.1, 130.1, 130.0, 129.9, 129.8, 129.7, 129.6, 129.4, 129.3, 129.2, 129.0, 128.8, 128.6, 128.4, 128.3, 128.2, 124.3, 124.1, 124.0, 123.4, 120.4, 101.1, 101.0, 99.5, 99.2, 96.5, 75.1, 73.2, 73.0, 72.2, 71.0, 69.7, 69.2, 63.6, 62.6, 60.5, 53.6 38.8, 23.2, 21.2, 14.3, 12.5, 10.6.

<4-6> Synthesis of RMA-C3E

According to the general procedure for a de-protection reaction in Example 1-7, RMA-C$_3$E was synthesized in 85% yield. $^1$H NMR (400 MHz, (CD$_3$)$_2$SO) δ 7.58 (s, 4H), 5.89 (d, J=6.9 Hz, 4H), 5.55-5.40 (m, 8H), 5.10-4.89 (m, 16H), 4.61-4.38 (m, 8H), 4.31-4.19 (m, 8H), 4.09-3.97 (m, 16H), 3.87-3.78 (m, 4H), 3.75-3.52 (m, 8H), 3.51-5.39 (m, 16H), 3.21-3.12 (m, 16H), 3.16-2.94 (m, 8H), 2.44-2.31 (m, 8H), 0.94 (t, J=7.4 Hz, 12H); $^{13}$C NMR (100 MHz, (CD$_3$)$_2$SO): δ 153.4, 153.3, 137.4, 123.7, 102.7, 100.9, 79.5, 76.4, 75.1, 73.3, 73.0, 72.4, 69.9, 60.8, 60.5, 54.8, 48.6, 38.9, 22.4, 12.2; MS (MALDI-TOF): calcd. for $C_{100}H_{114}O_{56}$ [M+Na]$^+$ 2263.8312, found 2263. 8523.

<Preparation Example 5> Synthesis of RMA-C4E

<5-1> Synthesis of Compound A2

According to the general procedure for the synthesis of octol-resorcin[4]arene in Example 1-1, compound A2 was synthesized in 81% yield.

<5-2> Synthesis of Compound B2

According to the general procedure for the synthesis of tetramethylcavitand in Example 1-2, compound B2 was synthesized in 82% yield.

<5-3> Synthesis of Compound C2

According to the general procedure for the synthesis of tetrakis(bromomethyl)cavitand in Example 1-3, compound C2 was synthesized in 83% yield.

<5-4> Synthesis of Compound E2

According to the general procedure for the synthesis of tetrakis(hydroxyethoxymethyl)cavitand in Example 1-5, compound E2 was synthesized in 64% yield.

<5-5> Synthesis of RMA-C4Ea

According to the general procedure for a glycosylation reaction in Example 1-6, RMA-C4Ea was synthesized in 42% yield. $^1$H NMR (400 MHz, CDCl$_3$): δ 8.07 (d, J=7.2 Hz, 8H), 7.97 (d, J=7.1 Hz, 8H), 7.97-7.79 (m, 32H), 7.65 (d, J=7.2 Hz, 8H), 7.51-7.42 (m, 32H), 7.41-7.28 (m, 28H), 7.27-7.14 (m, 20H), 6.97 (s, 4H), 6.09 (t, J=10.0 Hz, 4H), 5.81-5.49 (m, 14H), 5.38-5.21 (m, 8H), 4.93-4.65 (m, 10H), 4.64-4.59 (m, 6H), 4.56-4.32 (m, 8H), 4.30-4.18 (m, 4H), 4.17-3.97 (m, 16H), 3.96-3.79 (m, 4H), 3.69-3.57 (m, 4H), 3.51-3.36 (m, 4H), 2.21-2.16 (m, 8H), 1.42-1.25 (m, 8H), 0.97 (t, J=7.1 Hz, 12H); $^{13}$C NMR (100 MHz, CDCl$_3$): δ 171.2, 166.2, 165.9, 165.7, 165.5, 165.2, 165.1, 165.0, 154.2, 154.0, 138.0, 137.6, 133.6, 133.5, 133.4, 133.3, 133.1, 133.0, 130.1, 129.9, 129.8, 129.7, 129.6, 129.5, 129.3, 129.1, 129.0, 128.7, 128.5, 128.4, 128.2, 128.1, 123.6, 120.1, 101.0, 99.9, 98.1, 96.4, 75.0, 73.1, 72.9, 72.2, 71.0, 69.9, 69.4, 69.1, 63.4, 62.5, 60.5, 51.1, 36.3, 32.1, 21.1, 20.9, 14.2.

<5-6> Synthesis of RMA-C4E

According to the general procedure for a de-protection reaction in Example 1-7, RMA-C$_4$E was synthesized in 87% yield. $^1$H NMR (400 MHz, (CD$_3$)$_2$SO): δ 7.59 (s, 4H), 5.89 (d, J=6.9 Hz, 4H), 5.54-5.38 (m, 8H), 5.09-4.78 (m, 16H), 4.67-4.38 (m, 8H), 4.31-4.19 (m, 8H), 4.09-3.97 (m, 16H), 3.88-3.79 (m, 4H), 3.75-3.52 (m, 8H), 3.51-3.37 (m, 16H), 3.21-3.09 (m, 16H), 3.06-2.94 (m, 8H), 1.41-1.23 (m, 8H), 0.99 (t, J=7.4 Hz, 12H); $^{13}$C NMR (100 MHz, (CD$_3$)$_2$SO): δ 153.3, 137.5, 124.1, 121.9, 102.6, 100.7, 79.5, 76.3, 75.1, 73.3, 73.2, 72.9, 72.4, 69.9, 69.4, 67.6, 60.8, 60.5, 36.2, 31.1, 20.4, 13.8; MS (MALDI-TOF): calcd. for C$_{104}$H$_{152}$O$_{56}$ [M+Na]$^+$ 2319.8938, found 2319.8875.

<Preparation Example 6> Synthesis of RMA-C5E

<6-1> Synthesis of Compound A3

According to the general procedure for the synthesis of octol-resorcin[4]arene in Example 1-1, compound A3 was synthesized in 83% yield.

<6-2> Synthesis of Compound B3

According to the general procedure for the synthesis of tetramethylcavitand in Example 1-2, compound B3 was synthesized in 84% yield.

<6-3> Synthesis of Compound C3

According to the general procedure for the synthesis of tetrakis(bromomethyl)cavitand in Example 1-3, compound C$_3$ was synthesized in 85% yield.

<6-4> Synthesis of Compound E3

According to the general procedure for the synthesis of tetrakis(hydroxyethoxymethyl)cavitand in Example 1-5, compound E3 was synthesized in 64% yield.

<6-5> Synthesis of RMA-C5Ea

According to the general procedure for a glycosylation reaction in Example 1-6, RMA-C5Ea was synthesized in 45% yield. $^1$H NMR (400 MHz, CDCl$_3$): δ 8.07 (d, J=7.2 Hz, 8H), 7.98 (d, J=7.1 Hz, 8H), 7.91-7.73 (m, 32H), 7.65 (d, J=7.2 Hz, 8H), 7.51-7.40 (m, 32H), 7.39-7.28 (m, 28H), 7.27-7.14 (m, 20H), 6.97 (s, 4H), 6.10 (t, J=10.0 Hz, 4H), 5.81-5.49 (m, 14H), 5.38-5.21 (m, 8H), 4.93-4.65 (m, 10H), 4.64-4.59 (m, 6H), 4.56-4.32 (m, 8H), 4.30-4.19 (m, 6H), 4.17-3.97 (m, 16H), 3.96-3.79 (m, 4H), 3.70-3.59 (m, 4H), 3.53-3.38 (m, 4H), 2.24-2.17 (m, 8H), 1.51-1.19 (m, 16H), 0.92 (t, J=7.1 Hz, 12H); $^{13}$C NMR (100 MHz, CDCl$_3$): δ 171.3, 166.3, 165.9, 165.8, 165.6, 165.2, 165.1, 154.0, 137.8, 133.6, 133.5, 133.4, 133.3, 133.2, 133.1, 130.1, 130.0, 129.9, 129.8, 129.7, 129.6, 129.4, 129.2, 129.0, 128.8, 128.7, 128.6, 128.5, 128.3, 128.2, 123.7, 120.4, 101.0, 99.4, 96.5, 75.0, 73.0, 72.9, 72.5, 71.0, 70.0, 69.9, 69.5, 69.2, 63.6, 63.2, 62.6, 60.5, 53.6, 36.8, 30.2, 29.9, 22.9, 21.2, 20.9, 14.3.

<6-6> Synthesis of RMA-C5E

According to the general procedure for a de-protection reaction in Example 1-7, RMA-C5E was synthesized in 88% yield. $^1$H NMR (400 MHz, (CD$_3$)$_2$SO): δ 7.58 (s, 4H), 5.89 (d, J=6.9 Hz, 4H), 5.15-4.98 (m, 8H), 4.95-4.85 (m, 8H), 4.67-4.46 (m, 16H), 4.34-4.12 (m, 16H), 3.92-3.78 (m, 4H), 3.74-3.65 (m, 4H), 3.64-3.51 (m, 16H), 3.50-3.41 (m, 16H), 3.28-3.18 (m, 8H), 3.12-2.98 (m, 8H), 2.41-2.29 (m, 8H), 1.51-1.19 (m, 16H), 0.91 (t, J=7.4 Hz, 12H); $^{13}$C NMR (100 MHz, (CD$_3$)$_2$SO): δ 153.4, 137.6, 124.2, 102.7, 100.8, 99.4, 79.6, 76.4, 75.2, 73.5, 73.3, 73.0, 69.9, 69.5, 67.8, 62.3, 60.8, 60.5, 36.7, 30.0, 29.0, 22.2, 14.2; MS (MALDI-TOF): calcd. for C$_{100}$H$_{160}$O$_{56}$ [M+Na]$^+$ 2375.9564, found 2375.9355.

<Example 2> Method of Synthesizing Resorcinarene-Based Glucosides (RGAs)

Figure 2:
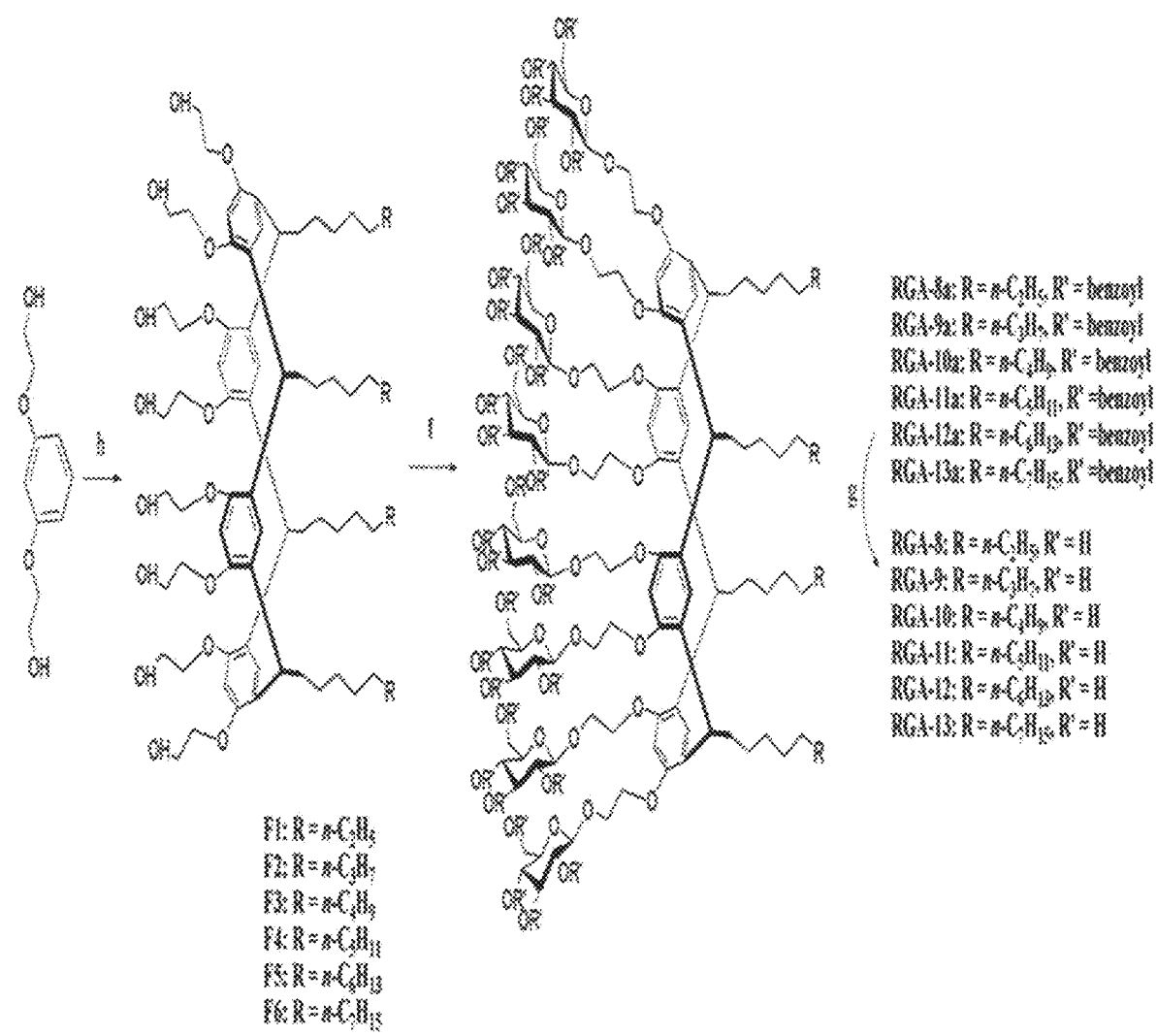
FIG. 2 is a diagram illustrating a synthesis scheme of RGAs according to Example 2 of the present invention.

A synthesis scheme of RGAs is shown in FIG. 2. Six types of RGAs were synthesized according to the following synthesis methods <2-1> to <2-3>. The synthesized RGAs are shown in FIG. 3.

<2-1> General Procedure for the Synthesis of octa-2-hydroxyethoxy Tetraalkylresorcinarene (Step h of FIG. 2)

1,3-bis(2-hydroxyethoxy) benzene (1.0 g, 0.005 mol) was added to a mixed solution of 1.5 ml of ethanol and 2 ml of concentrated HCl. To the resultant mixture, an aldehyde (0.005 mol) was added at 0° C. over 15 minutes. After stirring at room temperature for 15 minutes, the reaction mixture was transferred to an oil bath preheated at 90° C. and heated for 48 hours while stirring. After completion of the reaction (as detected by TLC), the reaction mixture was extracted using ethyl acetate and washed with water (2×30 mL) and brine. An organic layer was dried with anhydrous $Na_2SO_4$ and concentrated using a rotary evaporator. The residue was purified by column chromatography, thereby obtaining compound F as a white crystal solid.

<2-2> General Procedure for Glycosylation Reaction (Step f of FIG. 2)

Glycosylation was carried out according to the synthesis method (*Nat. Methods* 2010, 7. 1003.) written by P. S. Chae et al. To a solution in which an alcohol derivative (compound F) was stirred in $CH_2Cl_2$ (15 mL), 2,4,6-collidine (maltose (3.0 equiv.) or glucose (6.0 equiv.)) was added. AgOTf (maltose (5.0 equiv.) or glucose (10.0 equiv.)) was added to the resultant mixture at 0° C. After stirring for 10 minutes, a solution of perbenzoylated maltosylbromide (5.0 equiv. or 10.0 equiv.) dissolved in $CH_2Cl_2$ was slowly added thereto. The reaction was carried out for 30 minutes while stirring. After completion of the reaction (as detected by TLC), pyridine was added to the reaction mixture, and the mixture was diluted with $CH_2Cl_2$ (20 mL) before being filtered over Celite. A filtrate was washed with a 1 M aqueous $Na_2S_2O_3$ solution (40 mL), a 0.1 M aqueous HCl solution (40 mL), and brine (3×40 mL). An organic layer was dried with anhydrous $Na_2SO_4$, and a solvent was removed using a rotary evaporator. The residue was purified by silica gel column chromatography (EtOAc/hexane), thereby obtaining a maltose-glycosylated compound as a glassy solid.

<2-3> General Procedure for De-Protection Reaction (Step g of FIG. 2)

De-protection was carried out according to the synthesis method (*Nat. Methods* 2010, 7. 1003.) written by P. S. Chae et al. De-O-benzoylation was carried out under Zemplén's conditions. An O-protected compound was dissolved in anhydrous $CH_2Cl_2$ and then MeOH was slowly added thereto until precipitation continuously appeared. To the reaction mixture, a methanolic solution of 0.5 M NaOMe was added such that the final concentration was 0.05 M. The reaction mixture was stirred at room temperature for 6 hours. After completion of the reaction, the reaction mixture was neutralized with an Amberlite IR-120 ($H^+$ form) resin. The resin was removed by filtration, a filtrate was washed with MeOH, and a solvent was removed from the filtrate in vacuo. The residue was recrystallized using $CH_2Cl_2$/MeOH/ diethyl ether, thereby obtaining a purer de-O-benzolyated compound as a white solid. The compounds thus obtained are RGAs which are the compounds of the present invention.

<Preparation Example 7> Synthesis of RGA-8

<7-1> Synthesis of Compound F1

According to the general procedure for the synthesis of octa-2-hydroxyethoxy tetraalkylresorcinarene in Example 2-1, compound F1 was synthesized in 40% yield.

<7-2> Synthesis of RGA-8a

According to the general procedure for a glycosylation reaction in Example 2-2, RGA-8a was synthesized in 47% yield. $^1$H NMR (400 MHz, $CDCl_3$): δ 8.20-7.95 (m, 8H), 7.94-7.89 (m, 8H), 7.88-7.77 (m, 22H), 7.76-7.71 (m, 12H), 7.70-7.60 (m, 16H), 7.56-7.49 (m, 16H), 7.48-7.39 (m, 20H), 7.38-7.32 (m, 32H), 7.31-7.12 (m, 10H), 7.11-6.90 (m, 16H), 6.21-5.92 (m, 8H), 5.91-5.73 (m, 12H), 5.72-5.48 (m, 8H), 4.78-4.59 (m, 16H), 4.58-4.38 (m, 16H), 4.37-4.09 (m, 16H), 4.02-3.55 (m, 10H), 3.51-3.15 (m, 8H), 1.81-1.41 (m, 4H), 1.24-1.12 (m, 40H), 0.83 (t, J=7.6 Hz, 12H); $^{13}$C NMR (100 MHz, $CDCl_3$): δ 166.2, 166.0, 165.4, 165.3, 133.5, 133.3, 130.0, 129.9, 129.8, 129.2, 129.1, 128.5, 101.5, 73.4, 72.4, 72.2, 72.0, 70.0, 68.6, 63.1, 60.6, 32.4, 30.4, 29.8, 23.0, 21.3, 14.4.

<7-3> Synthesis of RGA-8

According to the general procedure for a de-protection reaction in Example 2-3, RGA-8 was synthesized in 87% yield. $^1$H NMR (400 MHz, $(CD_3)_2SO$): δ 6.67 (s, 4H), 6.65 (s, 4H), 5.10-4.79 (m, 24H), 4.61-4.38 (m, 12H), 4.21-4.19 (m, 8H), 4.18-3.92 (m, 12H), 3.91-3.82 (m, 8H), 3.81-3.60 (m, 16H), 3.58-3.39 (m, 8H), 3.38-3.22 (m, 16H), 3.21-3.13 (m, 16H), 3.05-2.92 (m, 4H), 1.81-1.59 (m, 8H), 1.20 (s, 40H), 0.83 (t, J=6.4 Hz, 12H); $^{13}$C NMR (100 MHz, $(CD_3)_2SO$): δ 154.5, 103.2, 103.1, 76.4, 73.4, 70.0, 67.8, 67.4, 61.0, 31.3, 29.3, 28.6, 27.4, 22.0, 13.8; MS (MALDI-TOF): calcd. for $C_{120}H_{192}O_{56}$ $[M+Na]^+$ 2552.2068, found 2552.1887.

<Preparation Example 8> Synthesis of RGA-9

<8-1> Synthesis of Compound F2

According to the general procedure for the synthesis of octa-2-hydroxyethoxy tetraalkylresorcinarene in Example 2-1, compound F2 was synthesized in 42% yield.

<8-2> Synthesis of RGA-9a

According to the general procedure for a glycosylation reaction in Example 2-2, RGA-9a was synthesized in 47% yield. $^1$H NMR (400 MHz, $CDCl_3$): δ 8.21-7.95 (m, 8H), 7.94-7.87 (m, 8H), 7.86-7.77 (m, 22H), 7.76-7.71 (m, 12H), 7.70-7.61 (m, 16H), 7.55-7.48 (m, 16H), 7.47-7.38 (m, 20H), 7.37-7.32 (m, 32H), 7.31-7.11 (m, 10H), 7.10-6.90 (m, 16H), 6.20-5.91 (m, 8H), 5.91-5.71 (m, 12H), 5.70-5.48 (m, 8H), 4.78-4.59 (m, 16H), 4.58-4.38 (m, 16H), 4.37-4.09 (m, 12H), 4.02-3.55 (m, 10H), 3.51-3.11 (m, 8H), 1.72-1.51 (m, 4H), 1.24-1.08 (m, 48H), 0.84 (t, J=7.6 Hz, 12H); $^{13}$C NMR (100 MHz, CDCl$_3$): δ 166.2, 166.0, 165.2, 133.4, 133.3, 130.0, 129.9, 129.8, 129.7, 129.2, 129.1, 128.5, 101.4, 73.4, 72.4, 72.2, 72.0, 69.9, 68.6, 63.1, 53.6, 32.2, 30.5, 30.1, 29.9, 22.9, 14.3.

<8-3> Synthesis of RGA-9

According to the general procedure for a de-protection reaction in Example 2-3, RGA-9 was synthesized in 88% yield. $^1$H NMR (400 MHz, (CD$_3$)$_2$SO): δ 6.67 (s, 4H), 6.48 (s, 4H), 5.11-4.74 (m, 24H), 4.61-4.37 (m, 12H), 4.36-4.17 (m, 8H), 4.16-3.97 (m, 12H), 3.96-3.84 (m, 8H), 3.83-3.60 (m, 16H), 3.59-3.39 (m, 8H), 3.26-3.16 (m, 16H), 3.15-2.89 (m, 16H), 1.81-1.59 (m, 8H), 1.20 (s, 48H), 0.83 (t, J=6.4 Hz, 12H); $^{13}$C NMR (100 MHz, (CD$_3$)$_2$SO): δ 154.5, 103.2, 103.1, 76.6, 73.4, 70.0, 67.4, 61.0, 31.2, 29.3, 28.9, 28.7, 27.4, 22.0, 13.8; MS (MALDI-TOF): calcd. for C$_{124}$H$_{200}$O$_{56}$ [M+Na]$^+$ 2608.2694, found 2608.2463.

<Preparation Example 9> Synthesis of RGA-10

<9-1> Synthesis of Compound F3

According to the general procedure for the synthesis of octa-2-hydroxyethoxy tetraalkylresorcinarene in Example 2-1, compound F3 was synthesized in 44% yield.

<9-2> Synthesis of RGA-10a

According to the general procedure for a glycosylation reaction in Example 2-2, RGA-10a was synthesized in 46% yield. $^1$H NMR (400 MHz, CDCl$_3$): δ 8.17-7.92 (m, 8H), 7.91-7.85 (m, 8H), 7.84-7.75 (m, 22H), 7.74-7.70 (m, 12H), 7.69-7.59 (m, 16H), 7.54-7.47 (m, 16H), 7.46-7.36 (m, 20H), 7.35-7.30 (m, 32H), 7.29-7.14 (m, 10H), 7.13-6.88 (m, 16H), 6.15-5.89 (m, 8H), 5.88-5.70 (m, 12H), 5.69-5.48 (m, 8H), 5.19-4.91 (m, 10H), 4.82-4.61 (m, 8H), 4.37-4.09 (m, 16H), 4.02-3.55 (m, 10H), 3.51-3.11 (m, 8H), 1.72-1.50 (m, 4H), 1.24-1.08 (m, 56H), 0.83 (t, J=7.6 Hz, 12H); $^{13}$C NMR (100 MHz, CDCl$_3$): δ 166.2, 166.0, 165.9, 165.4, 165.3, 133.4, 133.3, 130.0, 129.9, 129.8, 129.7, 129.2, 129.1, 128.5, 101.5, 72.4, 72.2, 72.0, 70.0, 68.6, 63.1, 53.6, 35.3, 34.9, 32.2, 30.5, 30.2, 29.7, 28.4, 22.9, 22.2, 14.3.

<9-3> Synthesis of RGA-10

According to the general procedure for a de-protection reaction in Example 2-3, RGA-10 was synthesized in 88% yield. $^1$H NMR (400 MHz, (CD$_3$)$_2$SO): δ 6.67 (s, 4H), 6.48 (s, 4H), 4.98-4.75 (m, 24H), 4.55-4.36 (m, 12H), 4.34-4.17 (m, 8H), 4.16-4.02 (m, 12H), 4.01-3.78 (m, 12H), 3.77-3.60 (m, 16H), 3.57-3.39 (m, 8H), 3.25-3.16 (m, 16H), 3.15-2.89 (m, 16H), 1.82-1.59 (m, 8H), 1.20 (s, 56H), 0.83 (t, J=7.0 Hz, 12H); $^{13}$C NMR (100 MHz, (CD$_3$)$_2$SO): δ 154.5, 103.2, 103.1, 99.6, 76.7, 73.4, 70.0, 67.8, 67.4, 61.1, 35.0, 34.0, 31.2, 29.4, 29.1, 29.0, 28.6, 27.4, 22.0, 13.8; MS (MALDI-TOF): calcd. for C$_{128}$H$_{208}$O$_{56}$ [M+Na]$^+$ 2664.3320, found 2664.3345.

<Preparation Example 10> Synthesis of RGA-11

<10-1> Synthesis of Compound F4

According to the general procedure for the synthesis of octa-2-hydroxyethoxy tetraalkylresorcinarene in Example 2-1, compound F4 was synthesized in 44% yield.

<10-2> Synthesis of RGA-11a

According to the general procedure for a glycosylation reaction in Example 2-2, RGA-1a was synthesized in 45% yield. $^1$H NMR (400 MHz, CDCl$_3$): δ 8.20-7.96 (m, 8H), 7.95-7.87 (m, 8H), 7.86-7.78 (m, 22H), 7.77-7.72 (m, 12H), 7.71-7.61 (m, 16H), 7.57-7.50 (m, 16H), 7.49-7.40 (m, 20H), 7.39-7.33 (m, 32H), 7.32-7.14 (m, 10H), 7.13-6.90 (m, 16H), 6.18-5.87 (m, 8H), 5.86-5.69 (m, 12H), 5.68-5.43 (m, 8H), 5.21-4.79 (m, 8H), 4.78-4.59 (m, 10H), 4.58-4.38 (m, 8H), 4.37-4.09 (m, 16H), 4.08-3.55 (m, 16H), 3.51-3.11 (m, 4H), 1.76-1.56 (m, 4H), 1.49-1.08 (m, 64H), 0.84 (t, J=7.6 Hz, 12H); $^{13}$C NMR (100 MHz, CDCl$_3$): δ 166.2, 165.4, 133.3, 130.0, 129.9, 129.7, 129.3, 129.1, 128.5, 101.3, 73.5, 72.5, 72.3, 72.1, 69.9, 68.7, 63.1, 53.6, 32.2, 30.4, 30.0, 29.9, 22.9, 14.3.

<10-3> Synthesis of RGA-11

According to the general procedure for a de-protection reaction in Example 2-3, RGA-11 was synthesized in 87% yield. $^1$H NMR (400 MHz, (CD$_3$)$_2$SO): δ 6.67 (s, 4H), 6.49 (s, 4H), 5.57-4.79 (m, 24H), 4.61-4.38 (m, 12H), 4.36-4.20 (m, 8H), 4.18-4.03 (m, 12H), 4.02-3.81 (m, 12H), 3.78-3.61 (m, 16H), 3.57-3.41 (m, 8H), 3.40-3.34 (m, 16H), 3.15-2.89 (m, 16H), 1.82-1.59 (m, 8H), 1.21 (s, 64H), 0.83 (t, J=6.8 Hz, 12H); $^{13}$C NMR (100 MHz, (CD$_3$)$_2$SO): δ 154.6, 154.5, 125.7, 125.3, 103.2, 103.1, 99.6, 76.7, 73.4, 70.0, 68.3, 67.8, 67.4, 61.1, 35.1, 34.0, 31.2, 29.4, 29.2, 29.0, 28.7, 27.4, 22.0, 13.8; MS (MALDI-TOF): calcd. for C$_{132}$H$_{216}$O$_{56}$ [M+Na]$^+$ 2720.3946, found 2720.4314.

<Preparation Example 11> Synthesis of RGA-12

<11-1> Synthesis of Compound F5

According to the general procedure for the synthesis of octa-2-hydroxyethoxy tetraalkylresorcinarene in Example 2-1, compound F5 was synthesized in 46% yield.

<11-2> Synthesis of RGA-12a

According to the general procedure for a glycosylation reaction in Example 2-2, RGA-12a was synthesized in 45% yield. $^1$H NMR (400 MHz, CDCl$_3$): δ 8.21-7.97 (m, 8H), 7.96-7.87 (m, 8H), 7.86-7.79 (m, 22H), 7.78-7.63 (m, 10H), 7.57-7.43 (m, 16H), 7.42-7.34 (m, 16H), 7.33-7.22 (m, 32H), 7.21-7.15 (m, 14H), 7.14-6.89 (m, 10H), 7.13-6.88 (m, 12H), 6.15-5.84 (m, 8H), 5.83-5.67 (m, 12H), 5.65-5.49 (m, 8H), 5.19-4.89 (m, 8H), 4.79-4.68 (m, 8H), 4.56-4.44 (m, 10H), 4.35-4.11 (m, 16H), 4.10-3.71 (m, 10H), 3.65-3.33 (m, 8H), 1.72-1.49 (m, 4H), 1.41-0.95 (m, 64H), 0.83 (t, J=7.6 Hz, 12H); $^{13}$C NMR (100 MHz, CDCl$_3$): δ 166.2, 166.0, 165.4, 165.3, 133.2, 130.0, 129.9, 129.2, 129.1, 128.5, 101.5, 73.4, 72.2, 72.0, 70.0, 63.2, 32.1, 30.4, 30.1, 30.0, 29.6, 22.9, 14.3.

<11-3> Synthesis of RGA-12

According to the general procedure for a de-protection reaction in Example 2-3, RGA-12 was synthesized in 89% yield. $^1$H NMR (400 MHz, $(CD_3)_2SO$): δ 6.67 (s, 4H), 6.48 (s, 4H), 5.01-4.79 (m, 24H), 4.57-4.38 (m, 12H), 4.32-4.18 (m, 8H), 4.17-4.02 (m, 12H), 4.01-3.82 (m, 12H), 3.79-3.61 (m, 16H), 3.58-3.41 (m, 8H), 3.28-3.17 (m, 16H), 3.16-2.89 (m, 16H), 1.81-1.59 (m, 8H), 1.21 (s, 72H), 0.83 (t, J=6.8 Hz, 12H); $^{13}$C NMR (100 MHz, $(CD_3)_2SO$): δ 154.6, 154.5, 125.7, 125.3, 103.2, 103.1, 76.7, 73.4, 70.0, 68.2, 67.4, 61.0, 35.1, 34.0, 31.2, 29.4, 29.2, 29.0, 28.6, 27.4, 22.0, 13.8; MS (MALDI-TOF): calcd. for $C_{136}H_{224}O_{56}$ $[M+Na]^+$ 2776.4572, found 2776.4949.

<Preparation Example 12> Synthesis of RGA-13

<12-1> Synthesis of Compound F6

According to the general procedure for the synthesis of octa-2-hydroxyethoxy tetraalkylresorcinarene in Example 2-1, compound F6 was synthesized in 47% yield.

<12-2> Synthesis of RGA-13a

According to the general procedure for a glycosylation reaction in Example 2-2, RGA-13a was synthesized in 44% yield. $^1$H NMR (400 MHz, $CDCl_3$): δ 8.21-7.96 (m, 10H), 7.95-7.89 (m, 8H), 7.88-7.79 (m, 22H), 7.78-7.63 (m, 8H), 7.58-7.43 (m, 12H), 7.42-7.34 (m, 18H), 7.33-7.20 (m, 32H), 7.19-7.02 (m, 14H), 7.01-6.80 (m, 10H), 6.15-5.87 (m, 8H), 5.86-5.67 (m, 12H), 5.66-5.46 (m, 8H), 5.31-4.84 (m, 8H), 4.79-4.58 (m, 8H), 4.57-4.41 (m, 8H), 4.35-4.11 (m, 12H), 4.10-3.71 (m, 10H), 3.56-3.33 (m, 8H), 1.72-1.49 (m, 4H), 1.41-0.95 (m, 72H), 0.84 (t, J=7.6 Hz, 12H); $^{13}$C NMR (100 MHz, $CDCl_3$): δ 166.2, 166.0, 165.3, 133.3, 130.0, 129.9, 129.1, 128.5, 101.6, 73.4, 72.0, 69.9, 63.1, 32.1, 30.4, 30.2, 30.0, 29.6, 22.9, 14.3.

<12-3> Synthesis of RGA-13

According to the general procedure for a de-protection reaction in Example 2-3, RGA-13 was synthesized in 90% yield. $^1$H NMR (400 MHz, $(CD_3)_2SO$): δ 6.67 (s, 4H), 6.47 (s, 4H), 5.01-4.79 (m, 24H), 4.61-4.39 (m, 12H), 4.34-4.20 (m, 8H), 4.17-4.01 (m, 12H), 3.99-3.82 (m, 12H), 3.79-3.61 (m, 16H), 3.58-3.41 (m, 8H), 3.25-3.17 (m, 16H), 3.16-2.95 (m, 16H), 1.81-1.59 (m, 8H), 1.20 (s, 80H), 0.83 (t, J=7.0 Hz, 12H); $^{13}$C NMR (100 MHz, $(CD_3)_2SO$): δ 154.6, 125.3, 103.2, 76.7, 73.4, 70.0, 68.2, 67.4, 61.1, 31.2, 29.0, 28.6, 27.4, 22.0, 13.8; MS (MALDI-TOF): calcd. for $C_{140}H_{232}O_{56}$ $[M+Na]^+$ 2832.5198, found 2832.5007.

<Experimental Example 1> Characteristics of RGAs and RMAs

To investigate the characteristics of RGAs and RMAs of Preparation Examples 1 to 12 synthesized according to the synthesis method of Examples 1 and 2, molecular weights (M.W.) and critical micelle concentrations (CMCs) of RGAs and RMAs and hydrodynamic radii ($R_h$) of formed micelles were measured.

Specifically, critical micelle concentrations (CMCs) were measured using a fluorescence dye, diphenylhexatriene (DPH), and hydrodynamic radii ($R_h$) of micelles formed of each compound (1.0 wt %) were measured by a dynamic light scattering (DLS) experiment. Measured results are shown in Table 1 in comparison with values of DDM as an existing amphipathic molecule (detergent).

TABLE 1

| Detergent | M.W. | CMC (M) | CMC (wt %) | $R_h$ (nm) |
|---|---|---|---|---|
| RGA-C8 | 2530.8 | ~10 | ~0.025 | 2.8 ± 0.1 |
| RGA-C9 | 2586.9 | ~7 | ~0.018 | 2.9 ± 0.1 |
| RGA-C10 | 2643.0 | ~5 | ~0.013 | 3.5 ± 0.2 |
| RGA-C11 | 2699.1 | ~3 | ~0.0081 | 6.8 ± 0.2 |
| RGA-C12 | 2755.2 | ~2.5 | ~0.0069 | 3.0 ± 0.2 |
| RGA-C13 | 2811.3 | ~2 | ~0.0056 | 3.7 ± 0.1 |
| RMA-C3 | 2066.0 | ~30 | ~0.0062 | 5.5 ± 0.2 |
| RMA-C4 | 2122.1 | ~15 | ~0.0032 | 7.5 ± 0.2 |
| RMA-C5 | 2178.2 | — | — | 6.5 ± 0.6 |
| RMA-C3E | 2242.2 | ~15 | ~0.0034 | 3.6 ± 0.1 |
| RMA-C4E | 2298.3 | ~10 | ~0.0023 | 4.6 ± 0.1 |
| RMA-C5E | 2354.4 | ~8 | ~0.0019 | 5.4 ± 0.1 |
| DDM | 510.1 | 170 | 0.0087 | 3.4 ± 0.0 |

All RGAs and RMAs exhibited CMC values of 0.001 to 0.030 mM which is significantly lower than that of DDM (0.17 mM). Therefore, RGAs and RMAs easily formed micelles even at low concentrations, and thus even a smaller amount thereof may be used to exhibit the same or higher level of effects compared to DDM. In addition, the CMC values of RGAs and RMAs were decreased with an increasing alkyl chain length, which is considered to be caused by an increase in hydrophobicity due to an extending alkyl chain length. Overall, the sizes of micelles formed by RGAs and RMAs tended to increase with an increasing alkyl chain length. On the contrary, exceptionally, the sizes of micelles formed by RGA-C12 and RGA-C13 were decreased. It was confirmed that all RGAs except RGA-C11 formed micelles of smaller sizes than those formed by RMAs, which is considered to be caused by the fact that the shape of RGAs is more conical than that of RMAs. In addition, it was confirmed that all RGAs except RGA-C11 formed micelles of similar sizes to those formed by DDM, whereas most RMAs formed micelles of larger sizes than those formed by DDM.

Meanwhile, size distributions of the micelles formed by RGAs and RMAs were measured using DLS. As results, micelles of all of RGAs and RMAs were measured as forming a single population, indicating that the micelles are highly homogeneous (FIG. 4).

Based on these results, it can be confirmed that, since RGAs and RMAs of the present invention have a smaller CMC value than DDM, micelles are easily formed even upon use of a small amount of RGAs and RMAs, whereby self-assembly tendencies thereof are much greater than DDM; the sizes of the micelles formed by RGAs and RMAs vary depending on the type thereof; and the micelles formed by RGAs and RMAs are highly homogeneous.

<Experimental Example 2> Evaluation of Membrane Protein (UapA) Structure Stabilization Ability of RGAs and RMAs An experiment was carried out to measure the structural stability of a uric acid-xanthine/$H^+$ symporter (UapA) isolated from *Aspergillus nidulans* caused by RGAs and RMAs. The structural stability of UapA was measured using a sulfhydryl-specific fluorophore, N-[4-(7-diethylamino-4-methyl-3-coumarinyl)phenyl] maleimide (CPM).

Specifically, UapAG411V$_{1-11}$ (hereinafter, referred to as "UapA") was expressed in combination with GFP in *Saccharomyces cerevisiae* FGY217 strains and isolated into a sample buffer (20 mM Tris (pH 7.5), 150 mM NaCl, 0.03% DDM, and 0.6 mM xanthine) according to the method described in the paper (*Mol. Membr. Biol.* 2013, 30, 32-42) written by J. Leung et al. The membranes containing UapA were diluted to a final protein concentration of 2.8 mg ml$^{-1}$ in PBS (pH 7.4) supplemented with either 1% DDM or 1% RMAs or RGAs. The sample was incubated while gently inverting at 4° C. for 1 hour and an insoluble material was removed by centrifugation at 15,000 g at 4° C. for 1 hour. The supernatant was injected into a Superose 6 10/300 column and eluted with an elution buffer (containing 20 mM Tris-HCl (pH 7.5), 150 mM NaCl, and 0.03% DDM). The individual elution fractions were transferred to a 200 µl clear 96-well plate. The GFP fluorescence of each fraction was read using an excitation wavelength of 470 nm and an emission wavelength of 512 nm to evaluate the thermal stability caused by an individual amphipathic compound and DDM.

Figure 5A:
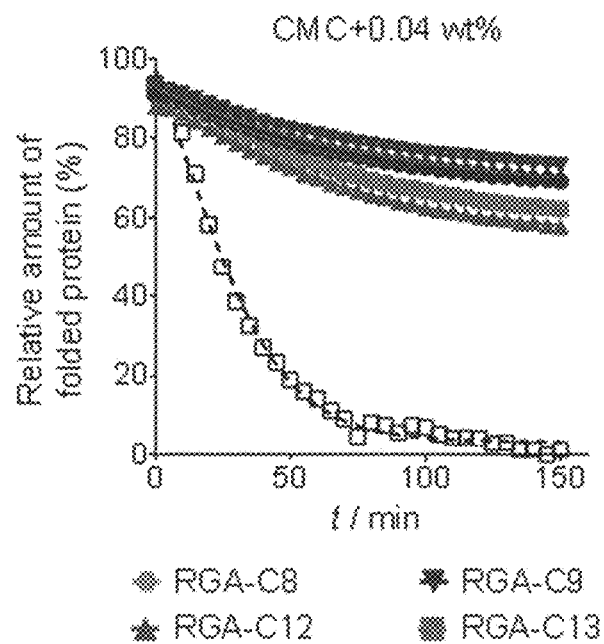
FIGS. 5A and 5B are a set of graphs illustrating a result of measuring the thermal stability of UapA in an aqueous solution caused by RGAs or DDM via fluorescence-detection size exclusion chromatography (FSEC)
Figure 5B:
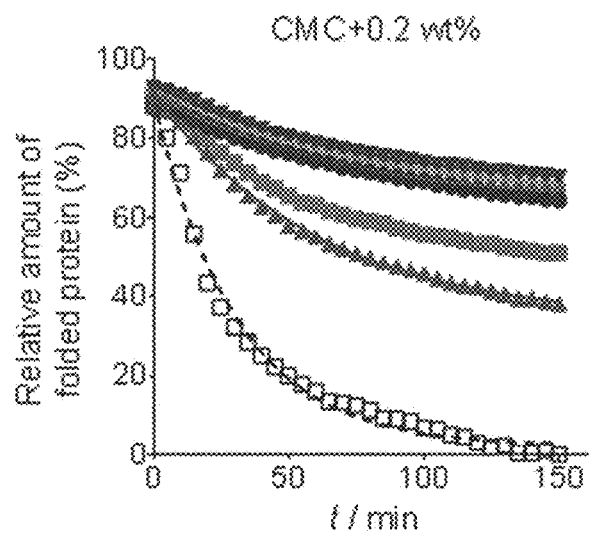
Figure 6A:
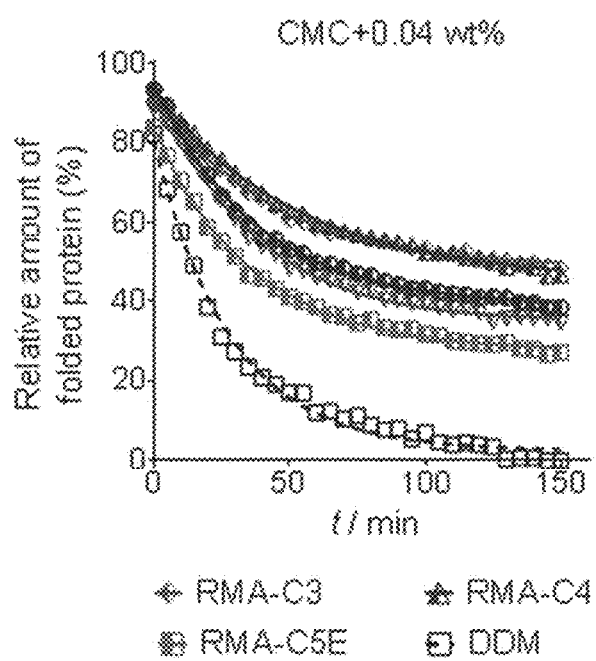
FIGS. 6A and 6B are a set of graph illustrating a result of measuring thermal denaturation profile of UapA protein in DDM and novel RMAs (RMA-Cs and RMA-CEs) used at CMC+0.04 wt % (a) or CMC+0.2 wt % (b). Protein stability was assessed by CPM assay carried out at 40° C. for 150 min.
Figure 6B:
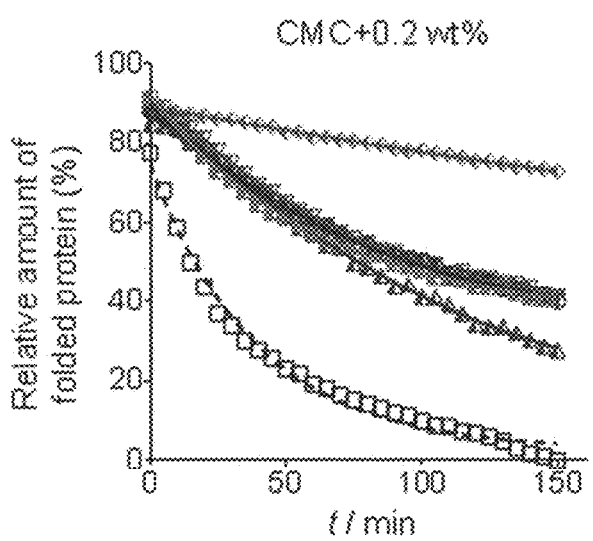

As shown in FIG. 5 and FIG. 6, it was confirmed that all of RGAs and RMAs exhibited an excellent ability to maintain the UapA protein in a folded state at all concentrations measured, compared to DDM. In particular, it was confirmed that RGA-C9 among RGAs exhibited the highest effect (FIG. 5) and RMA-C3 among RMAs exhibited the highest effect (FIG. 6).

Based on these results, it can be seen that RGAs and RMAs exhibited an excellent effect of maintaining UapA extracted from a cell membrane in a structurally stable state in an aqueous solution, and thus can be effectively used to stabilize a membrane protein.

<Experimental Example 3> Evaluation of Membrane Protein (LeuT) Structure Stabilization Ability of RGAs and RMAs An experiment was carried out to measure the structural stability of a leucine transporter (LeuT) caused by RGAs and RMAs. The concentrations of individual amphipathic compounds were (a) CMC+0.04 wt % or (b) CMC+0.2 wt %, and the substrate binding characteristic of LeuT was measured by scintillation proximity assay (SPA) using [$^3$H]-Leu. The measurement was carried out at regular intervals during 10 days of incubation at room temperature.

Specifically, wild type LeuT derived from *Aquifex aeolicus* which is a thermophilic bacterium was purified according to the method described in the paper (*Nature* 1998, 392, 353-358) written by G. Deckert et al. LeuT was expressed in *E. coli* C41 (DE3) transformed with pET16b encoding a C-terminal 8×His-tagged transporter (an expression plasmid was provided by Dr. E. Gouaux (Vollum Institute, Portland, Oreg., USA)). Briefly, the bacteria membrane was isolated and solubilized in 1% (w/v) DDM, then bound to a Ni$^{2+}$-NTA resin (Life Technologies, Denmark), and eluted with 20 mM Tris-HCl (pH 8.0), 1 mM NaCl, 199 mM KCl, 0.05% (w/v) DDM, and 300 mM imidazole. Subsequently, the purified LeuT (about 1.5 mg/ml) was diluted in the above buffer without DDM and imidazole, but supplemented with RGAs, RMAs (RMA-C3, RMA-C4, RMA-C3E, RMA-C4E, and RMA-C5E) or DDM to a final concentration of CMC+0.04% (w/v) or CMC+0.2% (w/v). The protein samples were stored at room temperature for 10 days and centrifuged at designated time points, and protein characteristics were determined by measuring the binding capacity of [$^3$H]-Leucine using SPA. SPA was performed with 5 µl of the respective protein samples in a buffer containing 450 mM NaCl and each RGA or RMA (or DDM). Also, SPA was performed in the presence of 20 nM [$^3$H]-Leucine and 1.25 mg/ml copper chelate (His-Tag) YSi beads (Perkin Elmer, Denmark). For the individual samples, a [$^3$H]-Leucine binding degree was determined using a MicroB eta liquid scintillation counter (Perkin Elmer).

As shown in FIG. 7, all RGAs except RGA-C8 exhibited an excellent effect of maintaining the substrate binding characteristic of LeuT during the 10-day incubation compared to DDM. That is, most RGAs completely retained the substrate binding characteristic of a transporter for a long period even at a high concentration of a compound. On the other hand, in the case of DDM, a constant structural collapse of the solubilized transporter was observed as the concentration of a compound increased. When the concentration of a compound increased to CMC+0.2 wt %, a difference in a transporter stabilization effect between RGAs and DDM was more clearly distinguished (FIG. 7B). Particularly, it can be confirmed that RGA-C8 exhibited the highest effect of maintaining the substrate binding characteristic of LeuT at CMC+0.2 wt %. In particular, it can be confirmed that RGA-C8, which has a short hydrophobic group, exhibited an enhanced effect as concentration increased, whereas other RGAs exhibited a consistent effect regardless of concentration.

In addition, as shown in FIG. 8, it was confirmed as a result of measuring the effect of RMAs on maintaining the substrate binding characteristic of LeuT that there was a significant difference between RMA-Cs and RMA-CEs. RMA-CEs exhibited a higher transporter stabilization effect than DDM at all concentrations, whereas RMA-Cs, which did not have an ethylene glycol linker, generally exhibited a somewhat lower transporter stabilization effect. This is because, when the entire lengths of the compounds coincide with the width of the transporter, a protein is effectively stabilized. Therefore, it can be confirmed that the entire length of compound is important. That is, it might be judged that RMA-CEs unlike RMA-Cs have an ethylene glycol linker so as to be formed with a length suitable for stabilizing a transporter, and thus exhibits a high transporter stabilization effect.

These results suggest that the overall structure of RGAs and RMAs, particularly, the entire length thereof acts as an important factor for maintaining the structural stability of LeuT.

<Experimental Example 4> Evaluation of Membrane Protein (MelB) Structure Stabilization Ability of RGAs and RMAs RGAs were selected, and an experiment was carried out to measure the structural stability of a *Salmonella typhimurium* melibiose permease (MelB) caused by RGAs. A MelB protein was extracted from a membrane using RGAs or DDM, and the amount and structure of the protein thus extracted was then analyzed by performing SDS-PAGE and western blotting. In this case, the concentration of the used amphipathic compound was 1.5 wt %. The protein was extracted at four temperatures (0, 45, 55, and 65° C.) and then incubated at the same temperatures for 90 minutes. Subsequently, two kinds of performance of the compound, that is, protein extraction efficiency and protein stability were evaluated at the same time by measuring the amount of a protein which remained dissolved in an aqueous solution. The amount of a protein which was extracted and stabilized by an individual amphipathic molecule was expressed as a relative value (%) with respect to the amount of the entire protein included in a membrane sample not treated with an amphipathic molecule.

Specifically, a C-terminal 10-His-tagged *Salmonella typhimurium* melibiose permease ($MelB_{St}$) was expressed in *E. coli* DW2 cells (melB and lacZY) using plasmid pK95AHB/WT $MelB_{St}$/CH10. Cells were grown and membranes were prepared according to the method described in a paper (*Nat. Commun.* 2014, 5, 3009) written by A. S. Ethayathulla et al. A protein assay was carried out with a Micro BCA kit (Thermo Scientific, Rockford, Ill.). RGAs and DDM were evaluated to measure the stability of $MelB_{St}$ according to the protocol described in a paper (*Nat. Methods* 2010, 7, 1003-1008) written by P. S. Chae et al. The membrane sample (final protein concentration of 10 mg/mL) containing $MelB_{St}$ was incubated in a solubilization buffer containing 1.5% (w/v) DDM or RGAs (20 mM sodium phosphate, pH 7.5, 200 mM NaCl, 10% glycerol, and 20 mM melibiose) at four temperatures (0, 45, 55, and 65° C.) for 90 minutes. An insoluble material was removed by ultracentrifugation at 355,590 g at 4° C. for 45 minutes using a Beckman Optima™ MAX ultracentrifuge equipped with a TLA-100 rotor. A dissolved portion was separated by SDS-16% PAGE, and immunoblotting was then performed using a Penta-His-HRP antibody (Qiagen, Germantown, Md.). A membrane fraction containing 20 µg of protein without treatment was used to illustrate the overall MelB, and the treated samples were loaded into each well in equal volume. $MelB_{St}$ was measured using the SuperSignal West Pico Chemiluminescent substrate by ImageQuant LAS 4000 Biomolecular Imager (GE Healthcare Life Sciences).

As shown in FIG. 9, DDM exhibited high MelB protein extraction efficiency at 0 and 45° C. RGAs exhibited lower membrane protein solubilization efficiency than DDM at 0° C., and some RGAs (RGA-C11 and RGA-C13) exhibited protein extraction efficiency and protein solubility which are similar to those of DDM at 45° C.

However, when the temperature was raised to 55° C., RGA-C11 and RGA-C13 among RGAs efficiently extracted the MelB protein and maintained MelB solubility better than DDM. At 65° C., the MelB protein was hardly extracted in the case of all of DDM and RGAs.

It can be seen that DDM generally exhibited higher protein extraction efficiency than RGAs at a low temperature (0° C.), whereas RGA-C11 and RGA-C13 exhibited similar protein extraction efficiency to that of DDM at a relatively high temperature (45° C.) and higher protein extraction efficiency than DDM at a high temperature (55° C.), indicating that although DDM is excellent in protein extraction efficiency, RGA-C11 and RGA-C13 are superior to DDM in terms of protein stability.

<Experimental Example 5> Evaluation of Membrane Protein ($\beta_2$AR) Structure Stabilization Ability of RGAs and RMAs An experiment was carried out to measure the structural stability of a human (32 adrenergic receptor ($\beta_2$AR) and a G protein-coupled receptor (GPCR) caused by RGAs and RMAs. That is, a receptor purified with DDM was diluted with a buffer solution containing only each RGA and RMA without cholesteryl hemisuccinate (CHS) or a buffer solution containing CHS and DDM. The final concentration of the compound was CMC+0.2 wt %, and the ligand binding characteristic of the receptor was measured using [$^3$H]-dihydroalprenolol ([$^3$H]-DHA) binding.

Specifically, radioligand binding assay was carried out using the following method. $\beta_2$AR was purified using 0.1% DDM according to the method described in a paper (*Science*, 2007, 318, 1266-1273.) written by D. M. Rosenbaum et al. and finally concentrated to about 10 mg/ml (about 200 µM). The $\beta_2$AR purified with DDM was used to prepare a master binding mixture containing 10 nM [$^3$H]-dihydroalprenolol (DHA) supplemented with 0.5 mg/ml BSA in a 0.2% amphipathic compound (DDM, RGAs or RMAs). The receptor purified with DDM, RGAs or RMAs was incubated with 10 nM [$^3$H]-DHA at room temperature for 30 minutes. The mixture was loaded into a G-50 column, the flow-through was collected with 1 ml of a binding buffer (20 mM HEPES pH 7.5, 100 mM NaCl, supplemented with 0.5 mg/ml BSA and 20×CMC individual amphipathic compound, and the G-50 column was further filled with 15 ml of a scintillation fluid. Receptor-bound [$^3$H]-DHA was measured with a scintillation counter (Beckman). The binding capacity of [$^3$H]-DHA was measured and shown in a column graph. Each experiment was performed in triplicate.

In addition, a size exclusion chromatography (SEC) test was conducted. Specifically, $\beta_2$AR purified with 0.1% DDM was loaded on a M1 Flag column in the presence of 2 mM $CaCl_2$, and the column was washed with a DDM, RGA-C11 or RGA-C13 detergent buffer (20 mM HEPES pH 7.5, 100 mM NaCl, 0.2% individual amphipathic compound). The receptor was eluted with 20×CMC DDM, RGA-C11, or RGA-C13 with 5 mM EDTA and 0.2 mg/ml free Flag peptide. The eluate was further added to a Superdex-200 10/300 GL column (GE Healthcare) at 0.5 ml/min, and UV absorbance at 280 nm was recorded. The running buffer contained 20 mM HEPES pH 7.5, 100 mM NaCl, 20×CMC individual detergent (DDM, RGA-C11 and RGA-C13).

As shown in FIG. 10, in terms of maintaining the ligand binding characteristic of the receptor, RGA-C8 and C9 were inferior to DDM, RGA-C10 was similar to DDM, and RGA-C11, RGA-C12, and RGA-C13 were superior to DDM.

In addition, a test for identifying the effect of RGA-C11, RGA-C12, and RGA-C13 on maintaining the ligand binding of the receptor for a long period was conducted. Specifically, the ligand binding characteristic of the receptor dissolved in RGA-C11, RGA-C12, RGA-C13, or DDM was monitored at regular intervals during 2 days of incubation at room temperature, and results thereof are shown in FIG. 10B. As results, RGA-C12 exhibited an inferior ability to maintain the ligand binding of the receptor compared to DDM, whereas RGA-C11 and RGA-C13 exhibited a superior ability to maintain the ligand binding of the receptor compared to DDM at an early stage (from 0 to 12 h). Particularly, RGA-C13 exhibited receptor stability enhanced by almost three times.

As a result of the SEC test, as shown in FIG. 11, the size of a receptor-detergent complex formed of RGA-C11 or RGA-C13 was significantly smaller than that formed of DDM. The small receptor-detergent complex formed of RGA-C11 or RGA-C13 is advantageous for structure analysis through X-ray crystallography and electron microscopy (EM). It was believed that the formation of such a small complex resulted from the area characteristics of the molecule and was also caused by the presence of a relatively short alkyl chain. The receptor-detergent complex found in this test was very small, which had never been seen before.

As shown in FIG. 12, RMAs also exhibited a similar tendency to RGAs. RMA-C3E and RMA-C5E exhibited higher ligand binding characteristics compared to DDM, and, accordingly, the effect of RMA-C3E on maintaining the ligand binding of the receptor for a long period was identified. As results, it was confirmed that RGA-C3E had an ability to maintain the ligand binding of the receptor twice as high as that of DDM at an early stage.

What is claimed is:

1. A compound represented by the following Formula 1 or Formula 2:

[Formula 1]

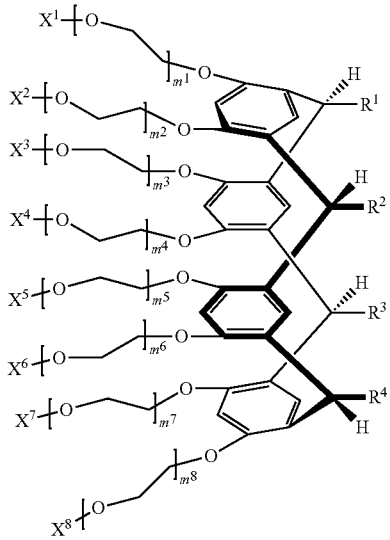

wherein $R^1$ to $R^4$ are each independently a substituted or unsubstituted C2-C30 alkyl group, a substituted or unsubstituted $C_3$-$C_{30}$ cycloalkyl group, or a substituted or unsubstituted $C_3$-$C_{30}$ aryl group;

$X^1$ to $X^4$ are saccharides; and $m^1$ to $m^4$ are 0, 1, or 2.

2. The compound of claim 1, wherein the saccharide is a monosaccharide or a disaccharide.

3. The compound of claim 1, wherein the saccharide is glucose or maltose.

4. The compound of claim 1, wherein $R^1$ to $R^4$ are each independently said substituted or unsubstituted alkyl group; $X^1$ to $X^8$ are glucoses or maltoses; and $m^1$ to $m^8$ are 1.

wherein $R^1$ to $R^4$ are each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^8$ are saccharides; and $m^1$ to $m^8$ are 0, 1, or 2,

[Formula 2]

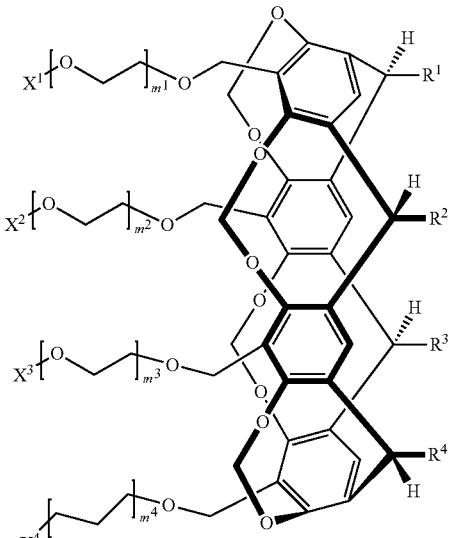

5. The compound of claim 1, which is a compound represented by one of the following Formulas 3 to 14:
[Formula 3]
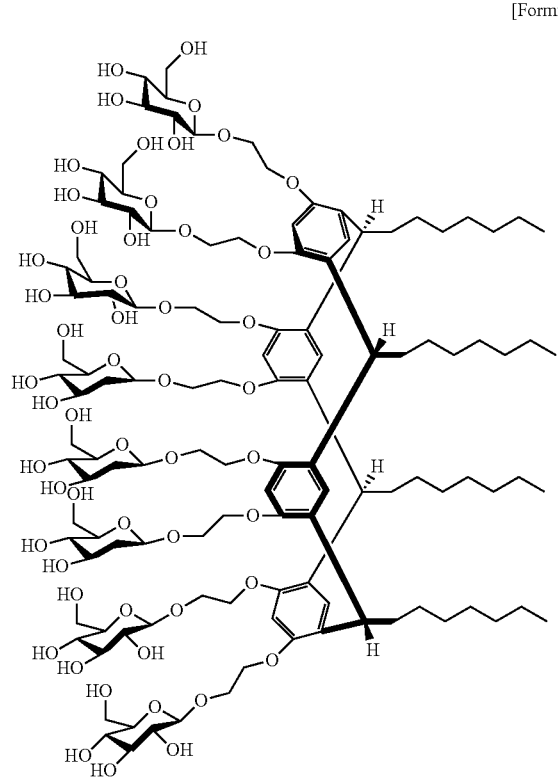
[Formula 4]
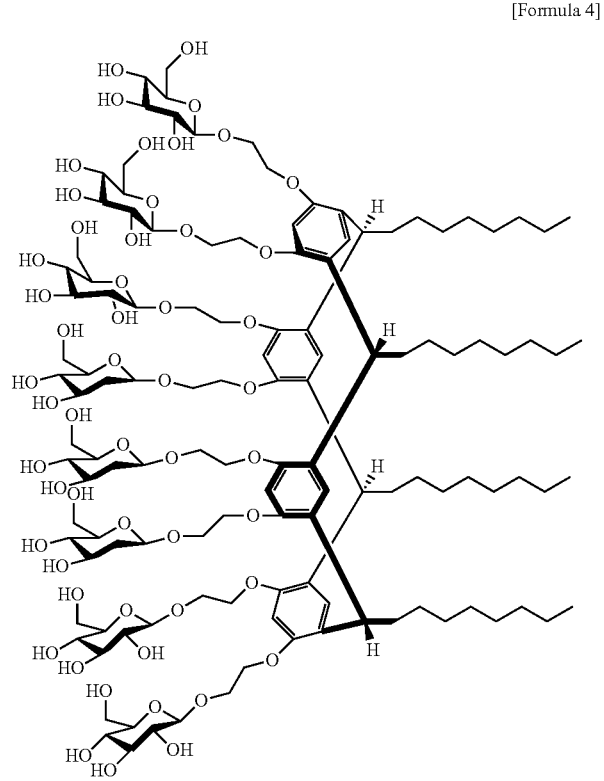
[Formula 5]
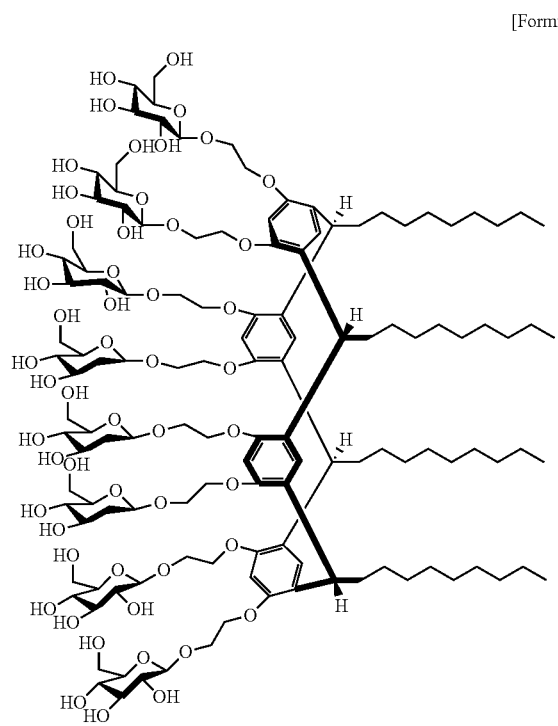
[Formula 6]
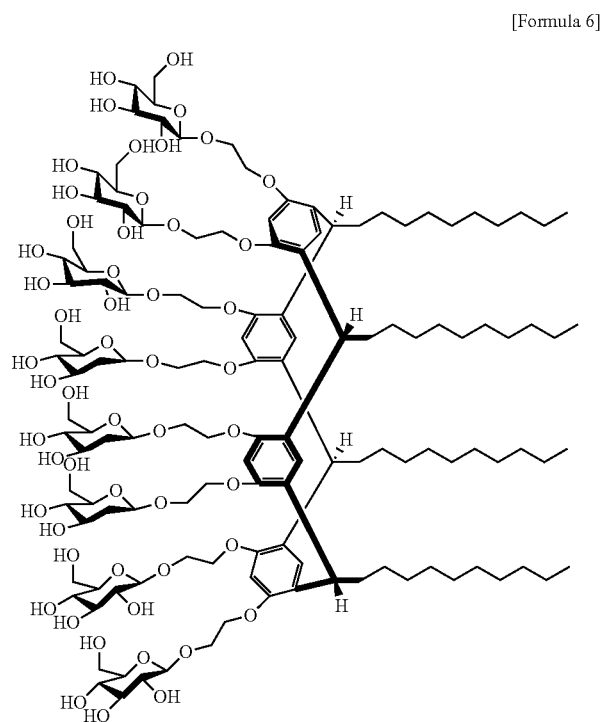

[Formula 7]
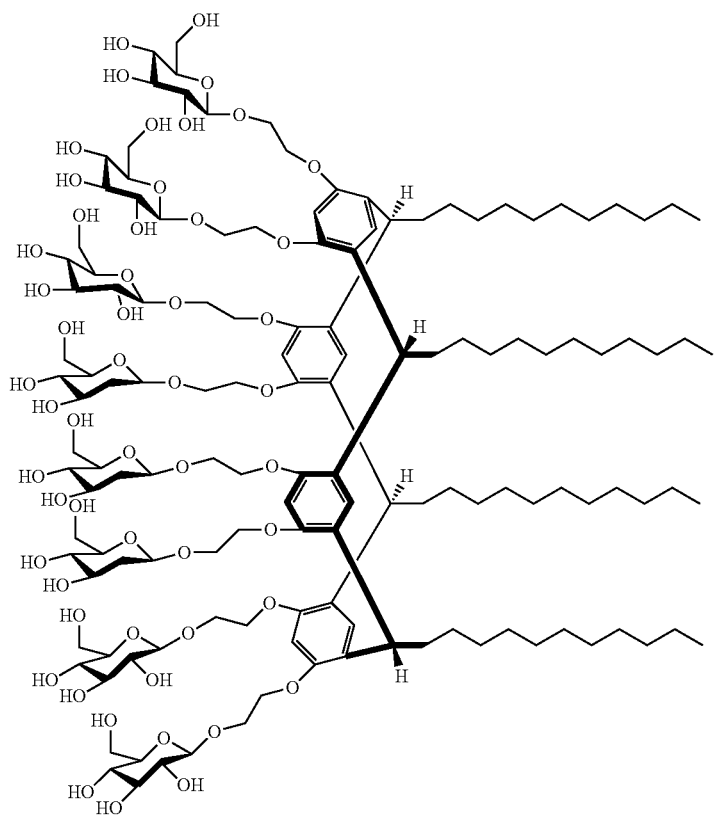
[Formula 8]
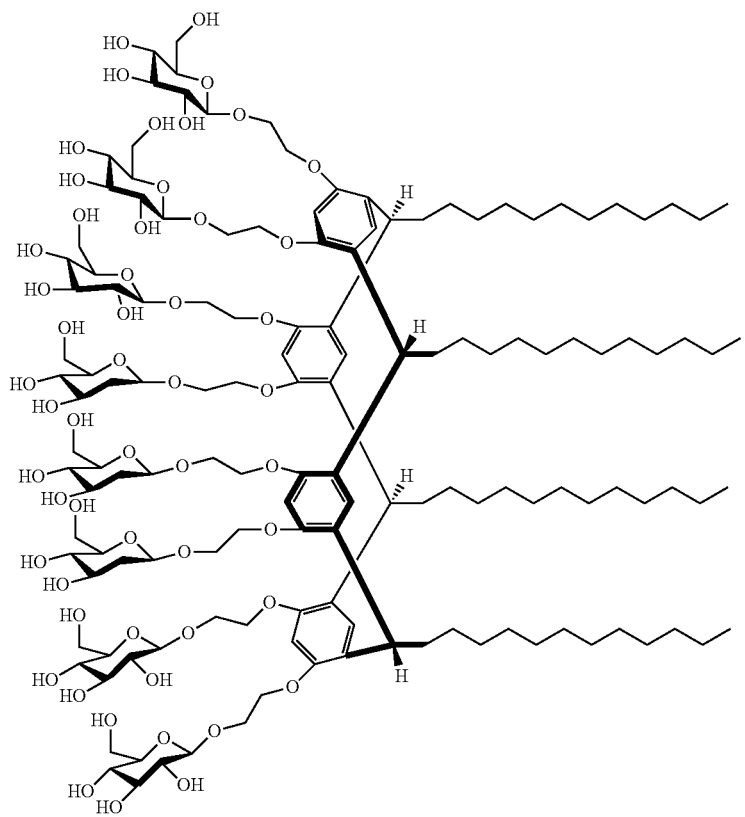

-continued
[Formula 9]
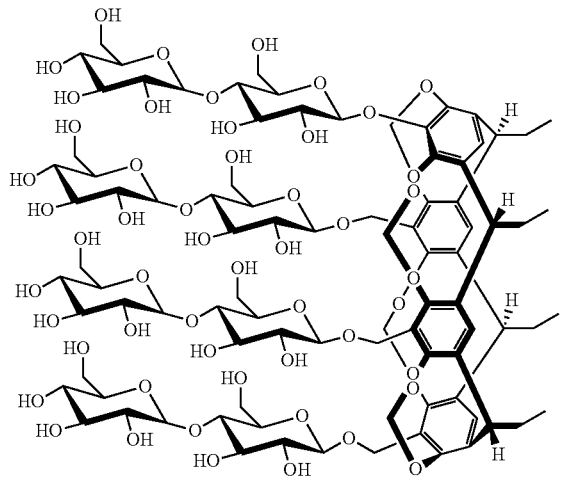
[Formula 10]
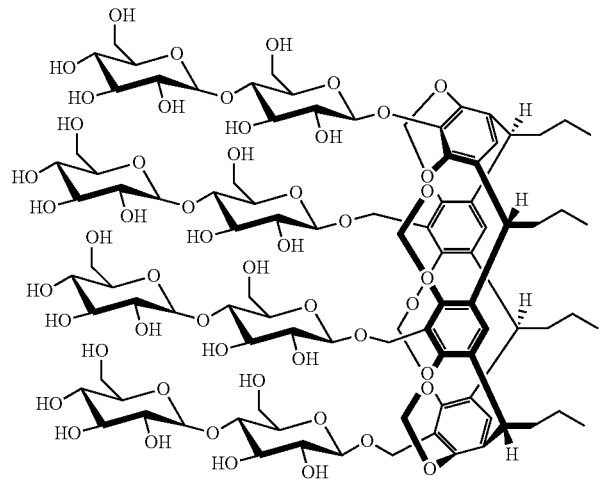
[Formula 11]
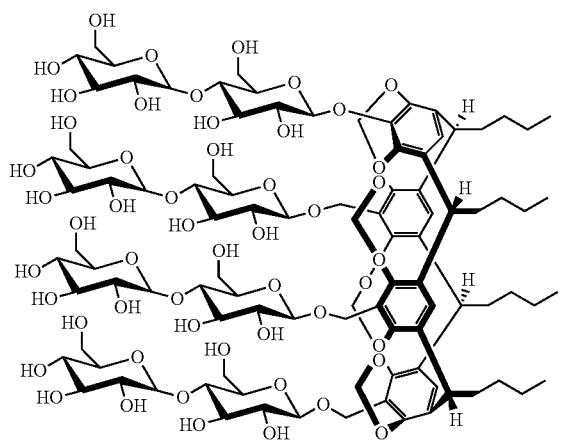
[Formula 12]
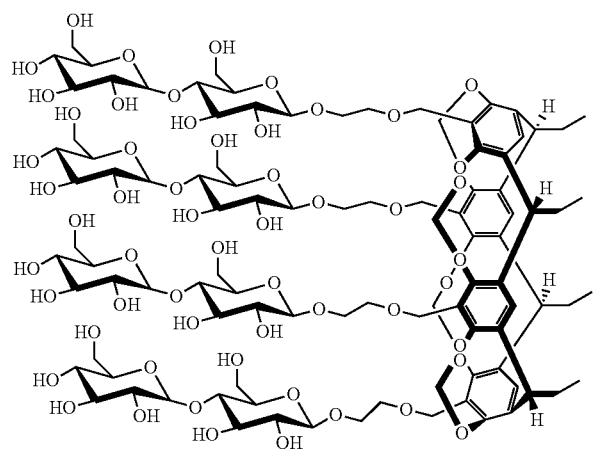
[Formula 13]
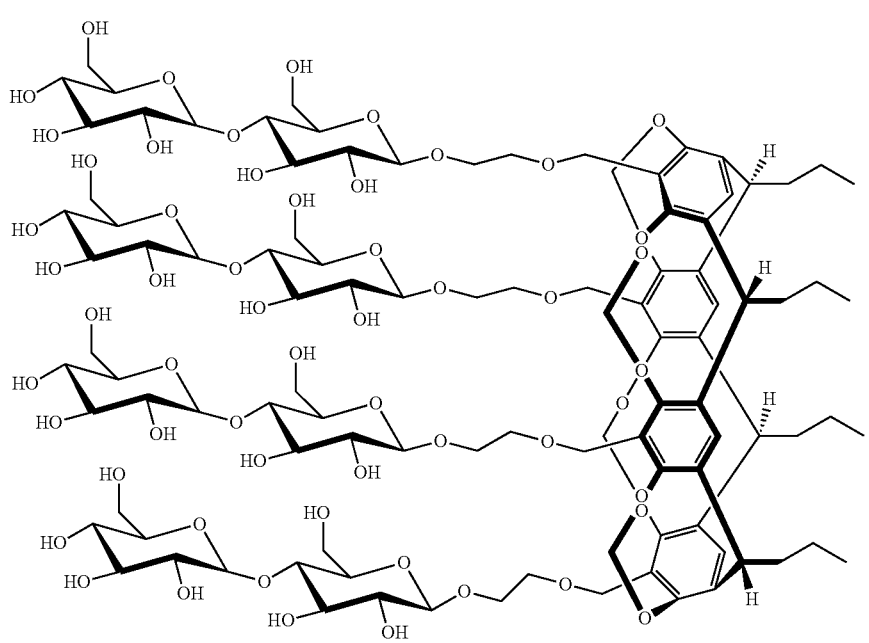

-continued

[Formula 14]

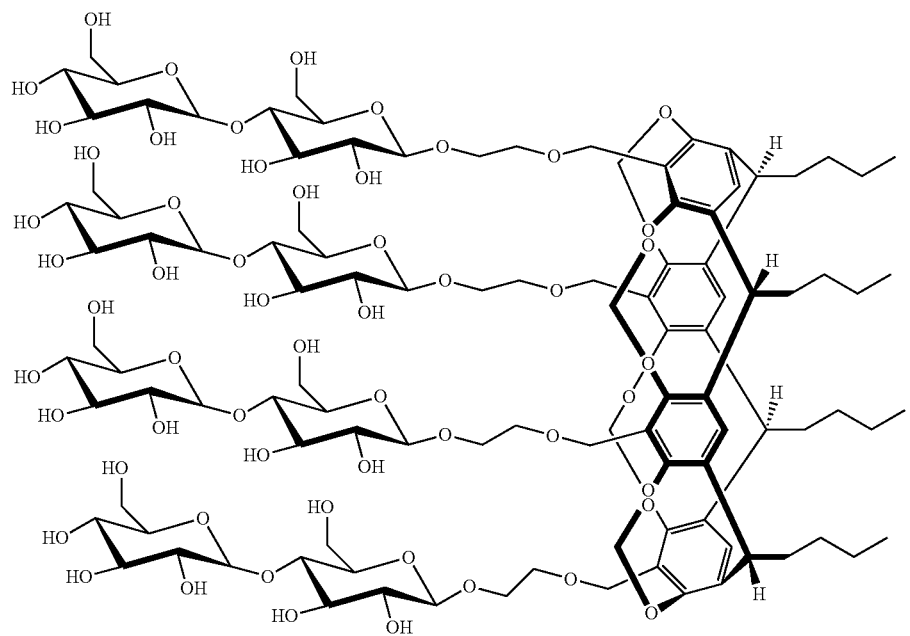

6. The compound of claim 1, wherein the compound is an amphipathic molecule for extracting, solubilizing, stabilizing, crystallizing, or analyzing a membrane protein.

7. The compound of claim 1, wherein the compound has a critical micelle concentration (CMC) of 0.0001 to 1 mM in an aqueous solution.

8. A composition for extracting, solubilizing, stabilizing, crystallizing, or analyzing a membrane protein, comprising the compound according to claim 1.

9. The composition of claim 8, wherein the composition is prepared in a form of micelles, liposomes, emulsions or nanoparticles.

10. A method of preparing a compound represented by the following Formula 1, comprising:

1) introducing an alkyl group by acid-catalyzed condensation of four 1,3-bis(2-hydroxyethoxy)benzene compounds;

2) introducing a protective group-attached saccharide by glycosylating the product of step 1); and 3) de-protecting the product of step 2):

[Formula 1]

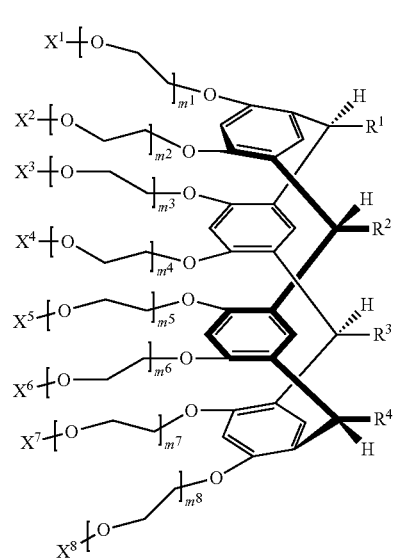

wherein $R^1$ to $R^4$ are each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^8$ are saccharides; and $m^1$ to $m^8$ are 0, 1, or 2.

11. The method of claim 10, wherein $R^1$ to $R^4$ are each independently a substituted or unsubstituted $C_3$-$C_{30}$ alkyl group; $X^1$ to $X^8$ are glucoses;

and $m^1$ to $m^8$ are 1.

12. A method of preparing a compound represented by the following Formula 2, comprising:
  1) introducing an alkyl group by acid-catalyzed condensation of four methyl resorcinol compounds;
  2) subjecting the product of step 1) to a methylene bridging reaction using bromochloromethane;
  3) brominating a benzylic position in the product of step 2);
  4) hydrolyzing or causing the product of step 3) to have ethylene glycol linkages;
  5) introducing a protective group-attached saccharide by glycosylating the product of step 4); and
  6) de-protecting the product of step 5):

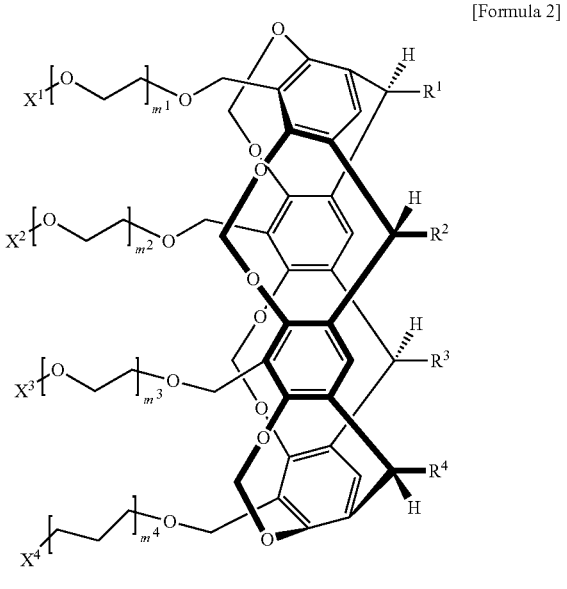

[Formula 2]

wherein $R^1$ to $R^4$ are each independently a substituted or unsubstituted $C_2$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^4$ are saccharides; and $m^1$ to $m^4$ are 0, 1, or 2.

13. A method of extracting, solubilizing, stabilizing, crystallizing, or analyzing a membrane protein, the method comprising treating a membrane protein with a compound represented by the following Formula 1 or Formula 2 in an aqueous solution:

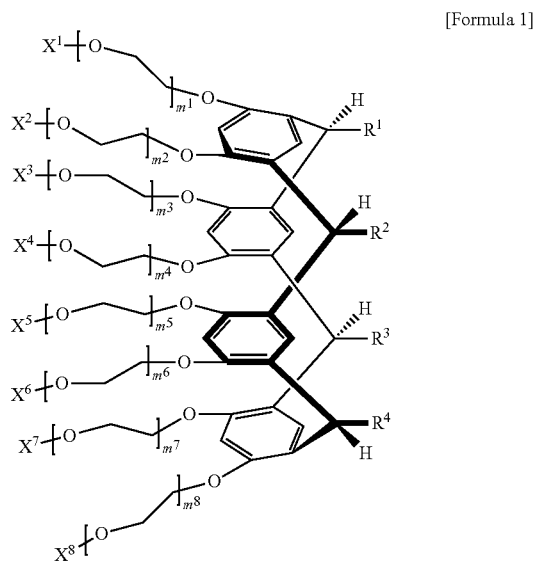

[Formula 1]

wherein $R^1$ to $R^4$ are each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^8$ are saccharides; and $m^1$ to $m^8$ are 0, 1, or 2,

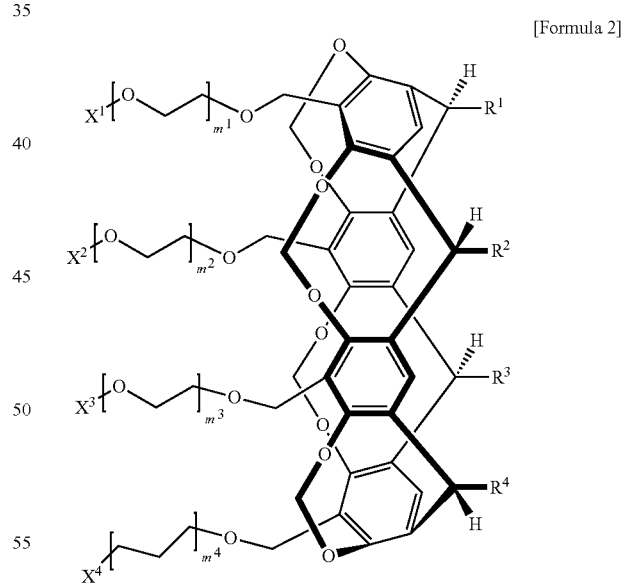

[Formula 2]

wherein $R^1$ to $R^4$ are each independently a substituted or unsubstituted $C_2$-$C_{30}$ alkyl group, a substituted or unsubstituted $C_3$-$C_{30}$ cycloalkyl group, or a substituted or unsubstituted $C_3$-$C_{30}$ aryl group;

$X^1$ to $X^4$ are saccharides; and $m^1$ to $m^4$ are 0, 1, or 2.

14. The method of claim 13, wherein $R^1$ to $R^4$ are each independently said substituted or unsubstituted alkyl group; $X^1$ to $X^8$ are glucoses or maltoses; and $m^1$ to $m^8$ are 1.

15. The method of claim 13, wherein the membrane protein is a uric acid-xanthine/Hxanthine/H$^+$ symporter (UapA), a leucine transporter (LeuT), a human $\beta_2$ adrenergic receptor ($\beta_2$AR), a melibiose permease (MelB), or a combination of two or more thereof.

* * * * *